United States Patent [19]

Slimak

[11] Patent Number: 5,244,689
[45] Date of Patent: Sep. 14, 1993

[54] FLOUR, BREAD, MILK, AND OTHER PRODUCTS FROM WHITE SWEET POTATOES CASSAVA, EDIBLE AROIDS, AMARANTH, YAMS, AND LOTUS

[76] Inventor: Karen M. Slimak, 9207 Shotgun Ct., Springfield, Va. 22153

[21] Appl. No.: 294,690

[22] PCT Filed: Feb. 2, 1987

[86] PCT No.: PCT/US87/00166

§ 371 Date: Aug. 1, 1988

§ 102(e) Date: Aug. 1, 1988

[87] PCT Pub. No.: WO87/04599

PCT Pub. Date: Aug. 13, 1987

Related U.S. Application Data

[63] Continuation-in-part of Ser. No. 824,786, Jan. 31, 1986, Pat. No. 4,911,943, and Ser. No. 825,655, Jan. 31, 1986, Pat. No. 4,923,709, and Ser. No. 825,656, Jan. 31, 1986, Pat. No. 4,925,697, and Ser. No. 825,658, Jan. 31, 1986, Pat. No. 4,925,696, and Ser. No. 825,659, Jan. 31, 1986, Pat. No. 4,946,703, and Ser. No. 825,660, Jan. 31, 1986, Pat. No. 4,929,467.

[51] Int. Cl.⁵ ............................................. A23L 1/214
[52] U.S. Cl. ..................................... 426/629; 426/94; 426/552; 426/523; 426/518; 426/633; 426/637; 426/640; 426/615
[58] Field of Search ................. 426/94, 629, 549, 615, 426/589, 633, 637, 640, 633, 658, 803, 518, 523

[56] References Cited

U.S. PATENT DOCUMENTS

| | | |
|---|---|---|
| Re. 29,773 | 10/1978 | Wisdom et al. ............... 426/49 |
| 38,039 | 3/1863 | Frost . |
| 77,995 | 5/1868 | Marshall . |
| 91,554 | 6/1869 | Marshall . |
| 100,587 | 3/1870 | Baylor . |
| 125,247 | 4/1872 | Adamson et al. . |
| 310,927 | 1/1885 | Whitcomb . |
| 592,906 | 11/1897 | Gere ........................... 426/640 |
| 1,119,849 | 12/1914 | Malcolm . |
| 1,151,805 | 9/1915 | Ray . |
| 1,193,828 | 8/1916 | Sattler . |
| 1,194,455 | 8/1916 | Williams . |
| 1,238,371 | 8/1917 | Williams . |
| 1,470,929 | 10/1923 | Yu Chen Li . |
| 1,571,945 | 3/1926 | Heimerdinger ............... 426/550 |
| 1,676,160 | 7/1928 | Ruffner . |
| 2,168,246 | 8/1939 | Shepherd . |
| 2,469,995 | 12/1946 | Schaul . |
| 2,687,960 | 8/1954 | Sharp . |
| 3,162,536 | 12/1964 | Kaufmann . |
| 3,208,855 | 9/1965 | Enoch et al. . |
| 3,346,390 | 10/1967 | Pichel ........................... 426/633 |
| 3,394,012 | 7/1968 | Kolton et al. . |
| 3,493,390 | 2/1970 | Succo ........................... 99/100 |

(List continued on next page.)

FOREIGN PATENT DOCUMENTS

| | | |
|---|---|---|
| 1517050 | 8/1974 | Fed. Rep. of Germany . |
| 2950315 | 6/1981 | Fed. Rep. of Germany . |
| 3141174 | 4/1983 | Fed. Rep. of Germany . |
| 1395654 | 2/1965 | France . |
| 2574633 | 6/1986 | France . |
| 104850 | 8/1980 | Japan ........................... 426/639 |

OTHER PUBLICATIONS

Weber "The Inca's answer to food shortages" Nature, United Kingdom (1978) vol. 272 pp. 486–502.

Foure et al. "Production & Marketing of composite flour bakery goods in developing countries" Proceedings IV Int'l Congress of Food Sci & Tech. (1974) vol. 5 pp. 231–242.

Ciacco "Tubers: composition & use in bread baking"

(List continued on next page.)

Primary Examiner—R. B. Penland
Attorney, Agent, or Firm—Stevens, Davis, Miller & Mosher

[57] ABSTRACT

Flours prepared from white sweet potatoes, cassava, edible aroids, tropical yams, lotus, arrowhead, buckbean, and amaranth, and a variety of different food products prepared from them, are substitutes for wheat and other grains, legumes, milk, eggs, and a partial substitute for nuts.

50 Claims, No Drawings

U.S. PATENT DOCUMENTS

| | | | |
|---|---|---|---|
| 3,497,360 | 2/1970 | Schaefer et al. | |
| 3,615,658 | 10/1971 | Glabe | 99/17 |
| 3,762,423 | 12/1973 | Tsantir et al. | 426/62 |
| 3,767,424 | 10/1973 | Shimizu et al. | 426/372 |
| 3,881,028 | 4/1975 | Caposella, Jr. et al. | 426/242 |
| 4,028,469 | 6/1977 | Kritchevskt et al. | 426/551 |
| 4,109,018 | 8/1978 | Thompson | 426/62 |
| 4,277,510 | 7/1981 | Wicklund et al. | 426/441 |
| 4,283,425 | 10/1981 | Yaun et al. | 426/102 |
| 4,520,034 | 5/1985 | Ishii et al. | 426/96 |
| 4,565,705 | 1/1986 | Snider | 426/640 |
| 4,749,574 | 6/1988 | Haydock et al. | 426/242 |
| 4,756,916 | 7/1988 | Dreher et al. | 426/302 |
| 4,853,236 | 8/1989 | Langler | 426/102 |
| 4,906,483 | 3/1990 | Kloos | 426/243 |
| 4,917,908 | 4/1990 | Prosise | 426/102 |
| 4,917,909 | 4/1990 | Prosise | 426/102 |
| 4,919,965 | 4/1990 | Childers, Jr. | 426/615 |
| 4,933,199 | 6/1990 | Neel et al. | 426/438 |

OTHER PUBLICATIONS

Dissertation Abstracts International B (1977) vol. 38 No. 4 p. 1480.

Snack Food Journal Feb. 1980 p. 20.

Winton et al. "The Structure and Composition of Foods" vol. II *Vegetables, Legumes,* Fruits John Wiley & Sons N.Y. 1935 pp. 120-123.

Sanchez-Marroguin "Amarenth Flour Blends & Fractions for Baking Applications" *J of Food Sci.* vol. 50 (1985) pp. 789-794.

Sanchez-Marroquin "Two forgotten crops of agroindustrial importance: amaranth & quinoa" *Chem. Abst* vol. 99 (1983) Abstract No. 103962p.

Cosier et al. "Bread production from pure flours of tropical starchy crops" *Tropical Foods:Chemistry & Nutrition vol. 1 Academic Press* N.Y. (1979) pp. 279-340.

Talburt et al. "Potato Processing" Avi Publishing Co (1959) pp. 390-391.

Ware "Possibilities in New and Extended uses of the sweet potato" Alabama Agricultural Experimental Station (1941) p. 9.

van de Mark "Alamalt—its properties & uses" *Alabama Agricultural Experimental Station* (1945) pp. 1-5.

Webster "Third New International Dictionary" PB Grove (Editor) Merriam Co. Publishers (1961) pp. 322, 500, 875, 2310 & 2457.

Bouwkamp "Sweet Potato Products: a natural resources of the Tropics" *CRC Press Inc.* pp. 137, 185-218, 255-258 (1985).

Bailey et al., Hortus Third, MacMillan Publishing Co., Inc., N.Y., pp. 683, 993, 773, 772, 757.

Beattie, W. R., 1908, Sweet Potatoes, Government Printing Office, Washington, pp. 34-37.

Bell et al., 1980, Effect of Traditional Food Processing Methods on the Nutritional Value of Yams in Camaroon in Tropical Root Crops: Research Strategies for the 1980s, ed. Terry et al., Nigeria, 218.

Bender, A. E., 1975, Dictionary of Nutrition and Food Technology, Chemical Publishing Co., Inc., N.Y., pp. 84-85.

Casier, J. P. J., 1975, Effect of Water Insoluble Endosperm Pentosans of Wheat and Rye on the Dough and Baking Properties of Soft Wheat and Other Starch Rich Materials such as Manionc, Sorghum, Millet, etc. *Fermentation,* 71:3, pp. 117-134.

Cassava Processing, 1977. The Food and Agriculture Organization of the United Nations, pp. 3, 12-15, 20-21, 84-85, 93-93.

Corwin, A. H., 1976, The rotating diet and taxonomy, in Clinical ecology, Dickey, L. H., ed., Charles C. Thomas Publisher, pp. 126-133.

Crabtree et al., 1978, The breadmaking potential of products of cassava as partial replacements for wheat flour, J. Fd Technol, vol. 13, pp. 397-407.

de Caloni et al., 1984, Elaboration and evaluation of typical Puerto Rican dishes prepared with mixtures of plantain, cassava and tanier flours, Jan. 1984, pp. 67-74. Food Engineering, pp. 250-262.

Ensminger et al., 1983, Foods and nutrition encyclopedia, vol. 1 A-H p. 2359.

Erdman, M. D., 1986, Starch from arrowroot (Maranta arundinacea) grown at Tifton, Ga., Cereal Chemistry, 63: 3, pp. 277-279.

Food composition tables for use in the English speaking Caribbean, 1974, The Caribbean Food and Nutrition Institute, Kingston, Jamaica, pp. 14-16.

Gleason, et al., Manual of vascular plants of Northeastern United States and adjacent Canada, D. van Nostrand Co., Inc., N.Y., p. 301.

Hudson et al., 1, The effects of fibre, starch damage and surfactants on the baking quality of wheat/cassava (List continued on next page.)

OTHER PUBLICATIONS composition flours, Journal of Food Technology, 2:2, pp. 129–136.

Yoshitaro, T., ed., 1942, Kenkyusha's new Japanese=English dictionary, Harvard university press, Cambridge, Mass. pp. 883, 884, 1586, 1587, 2152, 2153.

Martin et al., 1974, Flours made from edible yams (Dioscorea spp.) as a substitute for wheat flour, Journal of agriculture of University of Puerto Rico, pp. 255–263.

Martin, G. et al., 1983, Introduction of flour from *Dioscorea dumetorum* in a rural area, in Tropical root crops: production and uses in Africa, Proceedings of the Second Triennial Symposium of the International Society for Tropical Root Crops, Camaroon, pp. 161–163.

Morrison, F., 1957, Feeds and feeding: a handbook for the student and stockman, The Morrison Publishing Co., Ithaca, N.Y., pp. 390–393 556–557.

New Riverside University Dictionary, 1984, Houghton Mifflin Co., Boston, Mass., p. 1132.

The Oxford English dictionary, 1933, Oxford Univeristy Press, vol. 8, pp. 1315, 1318.

Peterson et al., 1968, A field guide to the wildflowers of Northeastern and Northcenral North American, Houghton Mifflin C., Boston, Mass., pp. 6, 8.

Pulle et al., 1975, Physico–chemical characterization of composite flours, Journal of Milk Food Technology, 38:7, pp. 401–405.

Raja et al., Studies on improving the textural quality of cassava (Tapioca) flour, pp. 108–116.

Rodriguez–Sosa et al., 1983, Amylography of plantain, cassava, and tanier flours, Journal of Agriculture of the University of Puerto Rico, pp. 303–311.

Sanchez–Marroquin et al., 1985, Industrial corn flour enrichment with whole amaranth flour and milling fractions in corn based products, Archivos Lationamericanso de Nutricion, 35:3, pp. 518–535.

Teutonico et al., 1985, Amaranth: composition, properties and applications of a rediscovered food crop, Food Technology, 39:4, pp. 49–61.

Agriculture Handbook No. 457, 1974(?), Tropical yams and their potential, part 1. *Dioscorea esculenta*, pp. 16–18.

Watt et al., 1963, Composition of foods: raw, processed, prepared, Agriculture Handbook No. 8, United States Department of Agriculture, Washington, D.C., pp. 66, 51.

Yanez et al., 1986, Amaranthus hypochondriacus: starch isolation and partial characterization, Cereal Chemistry, 63:3, pp. 273–277.

FLOUR, BREAD, MILK, AND OTHER PRODUCTS FROM WHITE SWEET POTATOES CASSAVA, EDIBLE AROIDS, AMARANTH, YAMS, AND LOTUS

REFERENCE TO RELATED APPLICATIONS

The present application is a continuation-in-part of U.S. patent applications Ser. Nos. 824,786; 825,655; 825,656; 825,658; 825,659; and 825,660, all filed on Jan. 31, 1986, now U.S. Pat. Nos. 4,911,943, 4,923,709, 4,925,697, 4,925,696, 4,946,703 and 4,929,467, respectively.

BACKGROUND OF THE INVENTION (1) Field of Invention

The present invention is concerned with the utilization of white sweet potatoes and all other light-fleshed tubers of the family Convolvulaceae, with the purpose of producing various flours from the tubers, and other valuable edible products and industrial products. Similarly, the present invention is concerned with producing flours and other valuable edible and industrial products from: 1) the tubers of the cassava and all other plants producing tubers of the family Euphorbiaceae; 2) tubers of malanga and all other plants producing tubers of the family Araceae; 3) the seeds of the amaranth, quinoa and all other seeds from the families Chenopodiaceae and Amaranthaceae, 4) the tubers of the yam and all plants producing tubers in the family Dioscoreaceae; and 5) the tubers of the lotus, arrowhead, buckbean and all other plants producing tubers in the families Nymphaeaceae, Alismataceae, and Gentianaceae.

(2) Description of The Background

Having food products available from as many different food sources as possible is of the greatest importance to persons with food allergies, and will become of even greater importance as food allergies are diagnosed in increasing numbers of people. As the potential problems of food allergies are more recognized, increasing numbers of people are looking for non-wheat items to include in their diets, to increase variety and aid in the prevention of food allergies.

Food allergies and intolerances have been known to exist for hundreds of years. The symptoms vary with each individual, and can include congestion, asthma, diarrhea, headaches, dizziness, joint pains, hives, eczema and in the most severe cases can cause anaphylaxis and even death. In recent decades, along with most other diseases related to the immune or auto-immune system, the incidence of food allergies has increased. In addition the number of foods to which a given individual reacts, and the severity of the reactions seems to be increasing. Indications are that food allergies will continue to become increasingly more common and severe.

The need for new food sources and alternatives parallels the increase in food allergies. As the number of foods an individual can eat begins to dwindle, it becomes increasingly more difficult to maintain a nutritious, well-balanced diet from the foods remaining, and the search for new foods intensifies. For many food allergy patients, the allergy problem steadily becomes more severe as the patient is unable to avoid becoming malnourished.

There is, then, a real need for alternatives to the food products that are the common and accepted staples in the American diet. These food products need to be from hypoallergenic foods so they have the best chance of being well tolerated by the greatest numbers of people. The hypoallergenic food products need to provide acceptable substitutes for the most hyperallergenic food products—wheat, corn, and other members of the grass family, legumes, milk and milk products, eggs, nuts, and yeast.

The alternative food products should be from less common or less well known foods. Such foods will have been eaten less often, if at all, and there will be a lower chance for a person to have developed allergies to the new foods. Products from such uncommon foods could probably be tolerated by most persons, and the risk of developing allergies to the foods would be lower.

The alternative food products need to be developed from foods in separate food families. This is important because food allergy patients can easily develop allergies to foods that are closely related to the foods they are already allergic to. New food products from as many new food families as possible (for example white sweet potato products from the morning glory family, cassava products from the spurge family, yam products from family Dioscoreaceae, and lotus from the water lily family), are much more needed than are food products from uncommon foods in a common food family (such as millet from the grass family). Alternative food products from food families not frequently included in peoples' diets will increase substantially the foods that people can eat in their rotation diets.

The alternative food products need to be highly concentrated foods. The above list of hyperallergenic foods includes most of the concentrated carbohydrates in the normal American diet. When people have to exclude these foods from their diets, the plant sources they have left to eat are primarily green leafy vegetables, tubers, and fruits. These food sources are high in fiber, but are relatively low in carbohydrates. A person who must rely on potatoes or sweet potatoes as their main source of carbohydrates, must eat about 5 pounds each day. It is very hard for many adults to eat this much food, but it is even more difficult for allergic children who may have to eat almost as much as an adult.

The alternative food products need to be as close to the eliminated foods as possible, in form and texture. For example, breads, pastas, cereal, cookies are needed from hypoallergenic sources, and these need to be as similar in taste and texture to their hyperallergenic counterparts as possible. This will make it possible for persons to enjoy foods they are used to, and will make them more likely to stay on their diets. Also people who are concerned that they may have food allergies are more likely to seek medical treatment if they know they will have pleasant alternatives in their diets.

Alternative food products are needed that consist of one primary ingredient, and this ingredient serves to replace wheat and other grains, milk, eggs, nuts, yeast, and sugar. The food allergies of individuals vary so greatly, that as the number of ingredients in a product increases, the number of individuals that can use the product decreases. Similarly, the products need to be free of additives, preservatives, and so forth, and should be completely free of pesticides and other chemicals.

Other characteristics that are important in new food products include convenience, portability, and variety. Many patients must change their diets at a time when they are very ill, and they simply do not have the strength to perform the food preparation needed when working with fresh fruits and vegetables.

Until now there has been no food product which could meet all of the above criteria. Many food products have been developed, but essentially all contain either wheat, or other grains, soy or legumes, milk, eggs, nuts, yeast, or sugar, or they do not have the characteristics of the common food products. Many specialty flours such as amaranth, have been combined with wheat flour to make new products, and these are not useful to the food allergic patient. Until now, it has not heretofore been possible to completely replace wheat products with a non-grain flour that also does not contain other main ingredients such as legumes, eggs, milk, sugar, and yeast, and also chemical modifiers.

In order to develop the needed alternative food products, it was first necessary to identify flours with suitable properties, and further with each of such flours, separately, as primary ingredient, to develop processes and techniques for preparing food products with properties and characteristics previously obtainable only from products containing wheat and other grains, legumes, eggs, milk, nuts and the like.

To find flours with suitable properties, existing flours of the art for sweet potatoes, cassava, malanga, yam, amaranth, quinoa, lotus, arrowhead, and buckthorn were evaluated. As is described below, using these art flours, other investigators had previously attempted to develop food products that were as completely non-grain in content as possible. In no case were these investigators able to prepare the desired food products without including other ingredients such as chemical modifiers, grain flours, high protein flours, eggs, milk, and the like. In most cases, prior investigators were able to use a non-wheat flour as a substitute for only a small percentage of the total amount of wheat flour in baked products. Uses of high carbohydrate flours to prepare substitutes for milk and milk products, eggs, and nuts is unknown.

Therefore it was necessary to develop new flours which could be more successfully used in the preparation of non-wheat flour products. Contrary to the teachings of the art, the applicant has found that when the dried tubers or seeds were comminuted to fine, relatively uniform particle size and wherein said relatively uniform particle size is obtained with greatly reduced amounts of sifting or without sifting, and thereby containing most or all of the plant fiber and other non-farinaceous material of the tuber or seed in the finely divided flour, there resulted a flour with unique and suprising properties, which was suitable for developing the desired processes and products.

These flours were found to each have unique and suprisingly different properties, and methods of preparation of each flour differ as well. Although no flour could be used in the same way as wheat flour, and although no two flours could be used in the same ways. It was possible to develop processes for each flour, and these processes were used to produce products comprising substantially one non-wheat flour ingredient with such products having properties and characteristics previously obtainable only from products containing ingredients selected from: wheat and other grains, legumes, eggs, milk, nuts, chemical modifiers, and the like.

New flour products with heretofore unobtainable properties have been developed from tubers of white or light fleshed sweet potatoes, cassava. malanga, tropical yams, lotus, arrowhead, and buckbean, and seeds of amaranth and quinoa. Each flour possesses different, unique, and suprising properties. Separate processes have been developed for each flour that allow its use as a substitute for grains, milk, and eggs, among other uses.

White sweet potatoes: The properties of flour and starch prepared from orange sweet potatoes are well known, and have been reported in the patent literature as early as the 1840's. Dried, ground orange sweet potatoes were patented for use as an ingredient in a coffee blend (U.S. Pat. No. 100,587 issued in 1870) because dried orange sweet potatoes look and taste like burned bricks. The caroteen pigment concentrates during drying and causes the disagreeable taste and color. The other patented uses of orange sweet potato flour are limited primarily to that of rehydratable powders primarily for use in orange sweet potato pie or pumpkin pies. This is probably due to the strong taste of orange sweet potato flour, the fact that when rehydrated, orange sweet potato flour loses cohesion, and will not keep a shape or hold trapped air. There are numerous mentions in the patent literature of processes for combining cooked or raw starches or flours from starchy tubers with various ingredients. Sweet potatoes (orange varieties) are frequently used as examples of 'other tubers'.

There is no reference to flours of white sweet potato varieties in the U.S. patent literature.

Several important teachings of the art have directed investigators completely away from any consideration of white sweet potatoes as possibilities for producing useful products.

Raw orange sweet potato flour made by the methods of Marshall (U.S. Pat. No. 77,995), and Baylor (U.S. Pat. No. 100,587) produced a flour considered inferior. The orange sweet potatoes tended to darken during dehydration; this darkened flour could not be rehydrated to make a good tasting substitute for the original fresh product, and the flour tended to have a very strong bitter taste, particularly when produced by the method of Baylor. Because of the inferior properties of raw orange sweet potato flour, in the late 1800's and early 1900's the field as a whole turned emphasis away from raw to cooked orange sweet potato flours. In the only mention of raw orange sweet potato flour since then, it is described as cattle fodder.

No orange sweet potato flour, whether raw or cooked, has been able to be used for more than about 30% of a wheat dough without significant deterioration in texture, risen structure, and taste. Even when a 15-85 mixture of orange sweet potato flour and wheat flour was used, the resulting bread product was significantly lower in specific volume. At ratios of 20-80, the specific volume of the bread product was reduced by 50 percent.

Other investigators have added cooked orange sweet potato flour to many products such as cookies, cakes, candies, ice cream, breads, and the like. In not one case was it possible to develop a product with orange sweet potato flour as the primary ingredient. It was only possible to add small amounts of cooked orange sweet potato flour to existing recipes containing conventional ingredients and to produce previously known products having orange sweet potato flavor and color.

White sweet potato flour is essentially an uninvestigated flour because fresh white sweet potatoes are considered (especially in the US) to be inferior to orange sweet potatoes. Sweet potatoes having white or light colored flesh are described as having poor quality and as being useful primarily for cattle fodder. If considered, the properties of white sweet potato flour would be expected to be less desirable than those of orange sweet potatoes. There would be no reason to suspect that a flour of white sweet potatoes could be prepared with properties greatly superior to flours of orange sweet potatoes. Thus the art teaches away from investigations on uses of white sweet potato flour.

In my early research on sweet potatoes, I tried making and using flours of orange sweet potatoes. The flavor of the raw orange sweet potato flour was very strong, as was described by other investigators. When I tried to use the flour to prepare pancakes and the like, the products fell apart in much the same way that fresh orange sweet potatoes tend to fall apart when they are cooked. In agreement with the teachings of the art, I was unable to prepare any products from orange sweet potato flour alone.

I then began to work with white sweet potatoes. In my early research on white sweet potato flour, the white sweet potato flour was made by a high speed impact method which produced a flour of wide particle-size distribution, with the fibrous portions of the tuber remaining in the larger particle sizes, and rendering the flour unsuitably heavy and gritty. When screened, (as is accepted practice in the art to obtain a fine flour) the larger particles (representing about $\frac{1}{4}$ of the total weight of the comminuted meal) were removed; this produced a lighter and less gritty flour, but one poorly suited for producing breads and other products where consistency and lightness are important. In addition it has been found that previous shreds had a high moisture content that made them susceptible to spoilage during dehydration and produced inferior products that spoiled easily.

I then developed a new process for preparing white sweet potato flour which involved reducing moisture content, incorporating more fibrous and non-farinaceous material into the flour and obtaining a more uniform particle size distribution in the flour. This flour had improved storage capability and provided products of palatable consistency. This flour, the flour of the instantly claimed invention, is suitable for use in baked and other products, and it was possible to develop new processes, different from conventions of the art, which made it possible to use the white sweet potato flour of the instantly claimed invention to prepare products with properties and characteristics previously only obtainable from products containing wheat and other grains, legumes, eggs, milk, nuts and the like.

Cassava: Cassava is a tuberous root of the Spurge family, Euphorbiaceae. As a fresh tuber it is boiled in salted water and consumed directly or after further frying or baking. It is used in soups stews, and the like, or it is mashed to a thick paste and fried. A variety of dried pulverized products are known including: a mash is fermented then dried to form a coarse, crunchy meal; the fibers are separated from the starch which is dried and powdered. The cassava starch, also called cassava flour, is similar in properties to cornstarch. It has quite high expansion capabilities when mixed with water and gelatinized, and is therefore used as a thickener, an agent to increase the rise of many products, and an agent to improve consistency and homogenicity. Their are many references to cassava starch or tapioca starch in the literature, and some references to cassava flour called tapioca flour. By their interchanging uses it is apparent that such uses generally refer to the starch product and not to the flour.

Prior to the instantly claimed invention, four flours of cassava were known. None of these flours have the properties of the instantly claimed invention; none can be used in the ways described for the instantly claimed invention. The two most common cassava flours are formed from cassava starch extraction processes: the starch and the extracted fiber mat. The third flour is a composite flour, i.e., a mixture of cassava flour and a high protein flour. The fourth flour is a whole flour of cassava.

Cassava starch also called cassava flour, tapioca starch, and tapioca flour, is an extract of starch from cassava pulp, that is dried and pulverized to a flour. Most literature references to cassava or tapioca flour are references to cassava starch. Cassava starch has been used as a substitute for up to 30% of the wheat flour content in wheat-based bread-type products, but it is not possible to substitute cassava starch for more than 30% of wheat in wheat-based baking products.

Cassava meal is a highly fibrous (often fermented) meal prepared from the dried pulp fiber by-product of cassava starch production. The particles of the meal are about $\frac{1}{2}$-1 mm in diameter. Gari, farinha, or mandioca are similar products of this type. Cassava meal is mixed with water and fried to produce a product called cassava bread. The bread is very hard and about $\frac{1}{4}$ inch thick. It exhibits no risen structure and is simply a hard mat of fibers. Other uses of the meal include mixing the meal with meats and gravies, preparation of a gruel, and sprinkling the meal over food.

Composite flours of cassava are combinations of cassava starch and high protein flours, such as peanut, soy, or wheat. Non-grain breads have been made from cassava composite flours. About a 30:70 ratio of high-protein flour to cassava starch is required, and chemical modifiers, fat, and sometimes malt are essential to successful preparation of the baked product. It has heretofore been possible to use only composite flours, not cassava flour alone, to produce non-wheat products of risen structure, and the risen structure-type products have only been possible from composite flours when chemical modifiers and fat are also used. Until the present invention it was thought that the protein content of and the levels of diastatic enzymes in, cassava flour or starch were too low, and that cassava flour alone could not be used to produce baked products of risen structure.

The whole cassava flour of the prior art is prepared from the portion of the cassava tuber that remains after the thick peel and the woody portions of the tuber are discarded. The pulverized meal is sieved as the final step to flour production; these steps remove substantial amounts of fiber from the final flour product. This cassava flour does not have the properties of the instantly claimed flour and cannot be used successfully as a primary flour to prepare baked products and the like.

No investigator has been able to use more than a 30% substitution of the above whole cassava flour for wheat flour in preparation of baked products, and whole cassava flour is considered greatly inferior to cassava starch. Until the present invention, it was generally thought that the fiber content of cassava flour strongly interferes with formation of risen structure.

The general teachings of the art which have directed investigators completely away from developing the cassava flours and the uses of the instantly claimed invention are as follows:

1) The art teaches that the best cassava flour for baking is one which has a high starch level and in fact is a starch.

2) The art teaches that tubers with the highest possible starch content and lowest possible fiber content are preferred as sources for flour. The least desirable, to the point of being unusable are post mature tubers where starch levels have dropped and lignification (resulting in highest possible fiber content) has occurred.

3) The art also teaches against the use of the entire substance of the cassava tuber. Indeed prior art teachings concerning processing steps for production of cassava flour, involve selective removal and discarding of the most fibrous portions of the cassava tuber. In the instantly claimed invention, the flours from such lignified tubers produce a flour with the best properties.

When processing cassava tubers, the art teaches that the fibrous, woody ends of the cassava tubers are to be cut off and discarded, also the low starch inner layer of the peel is usually discarded. These teachings produce flours with reduced levels of protein and fiber in comparison to the instantly claimed flour.

Cassava has a thick peel composed of a thin outer cork layer ($\frac{1}{2}$-2% of total weight of the tuber) and a thick inner layer composed of the phelloderm and phloem (8-15% of total weight of the tuber). On average, 25% of the root is discarded as skin and trimmings. Therefore the amount of highly fibrous material removed from cassava in trimming and removing the fibrous woody ends is about 10-15% of the total weight of the tuber.

Although if the outer cork layer of the skin is included in the instantly claimed flour product, its presence will not alter the unexpected benefits of the instantly claimed invention, the presence of the thin cork layer in the flour will interfere with the taste and color of the flour, and removal of the thin cork layer is preferred.

Even assuming that the maximum amount, 2%, of the cork layer is removed, and allowing 5% for removal of blemishes and the like, a total of about 18% of the cassava tuber that is normally discarded as inner peel and woody ends, is incorporated into the instantly claimed invention. (This percentage can rise to about 50% when post mature, lignified tubers are used in flour production.) The inner part of the peel, is known to contain only about half of the amount of starch of the core of the root and therefore contains greatly increased amounts of fiber. The highly woody ends of the roots are even lower in starch and higher in fiber than the inner layer of the peel.

4) The art also teaches that flour finishing steps of the art select for high starch and low fiber content of the finished flour. The art teaches that in processing flour, bolting or otherwise sieving is performed to produce a finer flour. A flour processed by screening or the like can not contribute the part removed by screening to the finished flour, and therefore the entire, thinly peeled substance of the tuber is not utilized. Screening processes significantly reduce the fiber content of the finished flour.

Sieving a cassava flour will reduce both the fiber content and the protein content. When the most coarse fraction of a cassava flour and the finest fractions are compared, the coarse fraction contains about 3.5 times the amount of fiber of the finest fraction, and the coarse fractions are much higher in protein as well.

5) The art teaches strongly that in preparing baked products, no more than 30% of the wheat flour ingredient may be replaced by cassava and that to achieve these levels requires the addition of shortening or oils, chemical modifiers, and the like.

6) The art finally teaches that non-wheat baked products of risen structure can not be prepared from cassava flour alone, and that baked products prepared from cassava flour are possible only when prepared from composite flours (comprised for example of cassava flour and a high protein pressed seed flour), and other essential ingredients including chemical modifiers and shortening.

Other than the above mentioned uses of cassava flour as an ingredient in baked goods, there have been very few attempts to develop food products from cassava flour. Pasta products have been prepared from composite flours containing cassava flour. Cassava starch is commonly used as a minor ingredient in ice cream.

The cassava flour of the instantly claimed invention has properties that are opposite to these teachings. The best flour is not a starch but rather a whole flour containing increased amounts of plant fiber and other non-farinaceous materials than are previously encountered. Tubers with high fiber content are preferred sources for the flour. Preferred processing steps incorporate woody parts and inner peel into the flour. The best flour comminutes all fibrous material into the flour. Preferred flours for baking are fine in particle size. Baked products from 100% cassava flour are made, and no other flours, chemical modifiers and the like are needed other than water and a leavening agent.

In my early research on cassava, the cassava flour was made by a high speed impact method which produced a flour of wide particle-size distribution, with the fibrous portions of the tuber remaining in the larger particle sizes, and rendering the flour unsuitably heavy and gritty. When screened, (as is accepted practice in the art to obtain a fine flour) the large particles were removed (this amounted to about $\frac{1}{4}$ of the flour product); this produced a lighter and less gritty flour, but one poorly suited for producing breads and other products where consistency and lightness are important. In addition it has been found that previous shreds had a high moisture content that made them susceptible to spoilage during dehydration and produced inferior products that spoiled easily.

I then developed a new process for preparing cassava flour which involved reducing moisture content, incorporating more fibrous and non-farinaceous material into the flour, and obtaining a more uniform particle size distribution in the flour. This flour had improved storage capability and provided products of palatable consistency. This flour, the flour of the instantly claimed invention, is previously not known. The properties of this flour are uniquely and suprisingly different from the previously existing flours. There would be no reason to suspect that the instantly claimed flour would have these properties. The new flour is suitable for use in baked and other products, and it was possible to develop new processes, different from conventions of the art, which made it possible to use the cassava flour of the instantly claimed invention to prepare products with properties and characteristics previously only obtainable from products containing wheat and other grains, legumes, eggs, milk, nuts and the like.

Malanga: Malanga represent one of the edible aroids of the family Araceae that includes taro, amorphophallus, tannia, yautia, eddo, cocoyam and many other species and varieties. They are widely consumed in Asia, Africa, Polynesia and Latin America, and they are almost exclusively eaten fresh by families who grow them. The term malanga, as used in this specification, is intended to include taro, amorphophallus, tannia, yautia, and the many other species and varieties.

There are few teachings of the art regarding any uses of edible aroids. The tubers are cooked and eaten, or the cooked tubers are pounded to a paste-like consistency and given to infants and the infirm. The paste is also used to make poi. The cooked tubers in a time-consuming process, are grated and combined with grated plantain or cassava. The mixture is stuffed with stew meat, and fried or wrapped in banana leaves and boiled in salted water. The final products are called pasteles or alcapurrias. Poi is dried and flaked to produce a product that can be rehydrated to produce an instant poi.

There are few references to malanga, taro, amorphophallus and other tubers of the family Araceae in the patent literature. U.S. Pat. No. 3,767,424 describes a method of separating starch from the tubers of *Amorphophallus konjac*, a tuber in the family Araceae. Starches from edible aroids produced by the above process and others are used commercially as thickening agents, in pharmaceutical products, and the like.

A very coarse flour (0.3 inch mesh) of tannia is the only whole flour of edible aroids known prior to the instantly claimed invention. The coarse flour was combined with water and rehydrated to form an edible food product whose properties are similar to those of the fresh tuber. This flour cannot be used according to the teachings of the instantly claimed invention to prepare products of risen structure and the like.

In the process for preparing the only flour known, the art teaches a process step of prolonged soaking. I find that the step of soaking in water greatly increases the water content of the tuber, prolongs the time period where conditions favor mold, and makes the drying materials highly susceptible to, and virtually unable to avoid, mold formation in the drying step. The instantly claimed invention teaches steps of minimizing soaking in water during peeling and during other process steps, immediate beginning of dehydration after shedding or otherwise comminuting, and achieving a dried product in the shortest possible time to avoid a sour taste in the dried product.

There is no teaching of the art regarding the use of malanga flour or the flour of other edible aroids in the preparation of baked products. Indeed, this use would not be possible with the only flour heretofore available.

The malanga flour of the instantly claimed invention is previously not known. The properties of this flour are uniquely and suprisingly different from the previously existing flours.

In my early research on malanga flour, I soaked the malanga tubers and then shredded them prior to dehydration. The soaking caused large portions of the drying shreds to spoil before becoming sufficiently dry and large amounts had to be discarded; the mold levels were unacceptably high in the dried product and palatability was poor. This problem was corrected by eliminating the step of soaking.

My first malanga flour product was prepared according to the conventions of the art. The flour contained a relatively wide particle-size distribution, with the fibrous portions of the tuber remaining in the larger particle sizes, and rendering the flour unsuitably heavy and gritty. When screened, (as is accepted practice in the art to obtain a fine flour) the large particles were removed; this produced a lighter and less gritty flour, but one poorly suited for producing breads and other products where consistency and lightness are important.

I then developed a new process for preparing malanga flour which involved reducing moisture content, incorporating more fibrous and non-farinaceous material into the flour, and obtaining a more uniform particle size distribution in the flour. This flour had improved storage capability and provided products of palatable consistency. This flour, the flour of the instantly claimed invention, is suitable for use in baked and other products, and it was possible to develop new processes, different from conventions of the art, which made it possible to use the malanga flour of the instantly claimed invention to prepare products with properties and characteristics previously only obtainable from products containing wheat and other grains, legumes, eggs, milk, nuts and the like.

Yam: There are no references to yam flours or products containing yams in the U.S. patent literature. Prior to the instantly claimed invention, flours of yam were known, however during processing from raw vegetable to dried flour, a powerfully strong and often strongly bitter taste was introduced. There is no mention in the literature of any interest in reducing the strong or bitter taste, nor of any investigations in this area. Rather there seems to be a matter of fact acceptance of this property of the flour. Emphasis is placed on helping consumers become accustomed to the taste, and on a search for a less bitter yam variety.

Prior to the instantly claimed invention, attempts were made by others to use the strong flavored or bitter flours of the art them in baked products. Such yam flours have been used in pancakes, cupcakes, rolls, and breads. Yam flour was substituted for 50% of the wheat flour in products of pancakes, cupcakes, and rolls, for 20% of the wheat flour in products of bread, and in one batch of cupcakes yam flour was substituted for 100% of the wheat flour. All such products included other ingredients such as milk, eggs, sugar, and the like. Such other ingredients were required to mask the disagreeable taste of the flour, as well as to contribute to needed texture and structure.

Other than the above mentioned uses of yam flour as an ingredient in baked goods, there are no known attempts to develop food products from yam flour.

There are no teachings regarding the use of such yam flour to prepare milk substitutes, egg substitutes, substitutes for nut, butters, or flour substitutes other than baked products of risen structure. There is further no teaching to suggest that such uses are possible.

To develop satisfactory uses for yam, processes for using the flour had to be developed, but these could not be used to prepare good tasting products unless a bland, non-bitter flour could be prepared.

As a first step in developing a non-bitter flour, the applicant began by observing that the traditional ways for cooking fresh yams involve relatively gentle, moist heat cooking techniques. When prepared in this manner, the yams are very bland and pleasant tasting; the taste and texture are difficult to distinguish from similarly cooked fresh potatoes. When high heat methods of cooking, particularly with oil, such as in frying, are used, the yam becomes strongly flavored or strongly bitter. When yams are baked, or air dried with heat (even low heat), they become strongly, disagreeably, bitter.

In processes of producing yam flour, the applicant has found that art recognized techniques of dehydration, such as air drying with heat or sun drying, resulted in the introduction of a strong flavor or bitter taste. Furthermore processes of comminuting dried yam to produce flour also caused the flour to turn strongly flavored or bitter.

As is known in the art, when yams are cooked prior to sun drying or air drying with heat, the cooked, dried yam shreds, pieces, or chips become less bitter than those of uncooked yam, but the bitter taste is still present. The cooked, dried shreds and the like are very hard and require harsh grinding conditions, e.g., longer grinding times and greater force applied, than is required for uncooked shreds. The applicant has found that the more harsh grinding conditions necessary for cooked, dried yam shreds causes the strong bitter taste to reappear. Therefore both cooked and uncooked dried yam flours of the are tend to be strong flavored and bitter.

The applicant has found that a good tasting, not bitter yam flour could be prepared when low temperature drying and grinding conditions were used to produce cooked and uncooked flours, and that these flours could then be used in baked products.

To produce a flour that could best be used in preparation of baked products and the like, it was further found that retaining as much of the fiber in the flour as possible improved the characteristics. The new, non-bitter yam flour, otherwise produced by the conventions of the art could not be used to prepare the desired products In my first attempts to prepare yam flour, the flour produced had a relatively wide particle-size distribution, with the fibrous portions of the tuber remaining in the larger particle sizes, and rendering the flour unsuitably heavy and gritty. When screened, (as is accepted practice in the art to obtain a fine flour) the large particles were removed; this produced a lighter and less gritty flour, but one poorly suited for producing breads and other products where consistency and lightness are important. In addition it has been found that previous shreds had a high moisture content that made them susceptible to spoilage during dehydration and produced inferior products that spoiled easily.

I then developed a new process for preparing yam flour which involved reducing moisture content, incorporating more fibrous and non-farinaceous material into the flour, and obtaining a more uniform particle size distribution in the flour. This flour had improved storage capability and provided products of palatable consistency. This flour, the flour of the instantly claimed invention, is suitable for use in baked and other products, and it was possible to develop new processes, different from conventions of the art, which made it possible to use the new yam flour to prepare products with properties and characteristics previously only obtainable from products containing wheat and other grains, legumes, eggs, milk, nuts and the like.

By these methods, a flour was produced that not only eliminated the problem of strong flavor or bitter taste, but which could also be used in novel processes to produce good tasting baked and other products wherein yam flour was not only the sole flour, but also was essentially the sole ingredient. Yam flour alone can be used to produce good tasting products, and added ingredients such as fat, eggs, milk, chemical modifiers and the like are not essential to preparation of acceptable products; although their use is not precluded.

A yam flour without a strong flavor or bitter taste and with the properties described above is unknown prior to the instantly claimed invention. No yam flour in the prior art has the properties of the instantly claimed invention; no yam flour in the prior art can be used in the ways described for the instantly claimed invention.

The general teachings of the art which have directed investigators completely away from developing the yam flours and the uses of the instantly claimed invention are as follows:

1) The art teaches that yam flours are disagreeable and strongly bitter in taste. This flavor carries into the finished, baked products rendering them strongly flavored or bitter or requiring the use of other ingredients to mask the taste.

2) The art also teaches that to successfully prepare baked products requires inclusion of other ingredients such as milk, sugar, eggs, chemical modifiers and the like.

3) The art finally teaches that even with the above ingredients, breads with satisfactory properties of 20–40% and higher yam flour content cannot be made, and that most other products can not be made at levels higher than 50%.

The yam flour of the instantly claimed invention has properties that are opposite to these teachings. The flour is not strongly flavored or bitter in taste. Baked products from 100% yam flour can be made, and no other flours, chemical modifiers, other ingredients, and the like are needed other than water and a leavening agent to make such baked products.

The yam flour of the instantly claimed invention is previously not known. The properties of this flour are uniquely and suprisingly different from the previously existing flours. There would be no reason to suspect that the instantly claimed flour would have these properties.

Amaranth: Amaranth flour products known prior to the instantly claimed invention are coarse, heavy, and grainy, the consistency of corn meal-type products. When used to produce products in which the heavy flour was the primary ingredient other than water or oil, the products were inferior in consistency, texture and palatability.

Prior to the instantly claimed invention, the following flours of amaranth are known: a coarse whole flour of amaranth, a fine sieved fraction of the coarse whole amaranth flour, and amaranth flours formed by pulverizing popped, toasted or parched amaranth. None of these flours have the properties of the instantly claimed invention; none can be used in the ways described for the instantly claimed invention.

1) Whole raw amaranth flour is a coarse meal of amaranth seeds. Amaranth seeds are very small, ranging from 0.9–1.5 mm in diameter, and they are very hard. The whole amaranth flours known in the art that are milled from raw amaranth are coarse, grainy and heavy, with a consistency similar to that of corn meal.

The finest whole amaranth flour previously known to the applicant prior to the instantly claimed invention is a flour in which amaranth seeds were milled and then sifted through a 40-mesh screen (aperture 0.425 mm). This particle size is very coarse for amaranth grains; a particle with a diameter one-third that of an unmilled seed would pass through this aperture. Such a flour is gritty and heavy, with the consistency of heavy corn meal. This flour is also sieved and therefore has different properties from truely whole amaranth flour.

When prior investigators used such amaranth flour in the preparation of bread products, the investigators were able to use such amaranth flour for up to 20% of the wheat flour in wheat-containing products without too great of an effect on overall properties; however, other ingredients including yeast, lard, sugar, malt, milk various emulsifiers, flavorings and the like were included in the products. No products were prepared without the added ingredients. Such amaranth flour can be used for as much as 50% of the wheat flour ingredient in cookies, pizza doughs, and short pasta, and as much as 5% in long pasta. These levels represent the upper limits of the teachings of the art regarding uses and possible substitutions of sifted, coarse, raw amaranth flours for wheat flours.

2) Fine, raw amaranth flour is the sifted, coarse raw amaranth flour described above that is further milled to a finer flour by bolting and sieving techniques. From a typical milling process, the following fractions are generally obtained: 52.6% 'bran', 20.1% broken grains, 16.2% coarse flour and 10.4% fine flour.

Other investigators have shown that fiber and protein contents of various flour fractions are significantly different. When the coarse amaranth meal is passed through an 80 mesh screen, the resulting flour fraction contains about 24-36% of the protein. A more coarse fraction, obtained by passing the coarse meal through a 60 mesh screen contained only 8-9% protein. Still finer amaranth flours can be made by passing the flour through a 100 mesh screen.

Fine amaranth flours comprise from about 10 to 30% of the original material of the seed. The finer the flour fraction, the greater the difference there is in protein content, fiber content and the like in comparison to the unmilled seed.

In prior attempts by other investigators to use amaranth flours in combination with wheat and other ingredients to prepare baked products, the more coarse fraction (40-60 mesh) was the preferred fraction, requiring reduced mixing times, and producing products with improved sensory properties and larger volumes. There is no suggestion in the teachings of the art that would direct one of ordinary skill in the art to explore the properties of finer, non-fractionated flours.

3) Popped, toasted, parched amaranth flours are produced by first popping, toasting or parching amaranth seeds, and then pulverizing to form a flour. These flours are prepared because amaranth is easier to mill after seeds have been treated with high heat, and thus finer flours can be prepared more easily. These flours are also subjected to the common particle size separations.

Although these flours may be easier to mill, the heat treatment processes result in changes in the structure of the seeds and resulting flour. These flours therefore are not well suited to the products and processes of the instantly claimed invention.

The general teachings of the art which have directed investigators completely away from developing the amaranth flours and the uses of the instantly claimed invention are as follows:

1) The art teaches that the best amaranth flour for baking is the coarse fraction sieved form the coarse whole amaranth flour.

2) The art teaches that in preparing baked products of risen structure, no more than 20% of the wheat flour ingredient may be replaced by whole amaranth. The art also teaches that amounts of amaranth flour varying from 5-50% may be substituted for wheat flours in selected products such as cookies, pizza dough, pastas, and the like.

3) The art finally teaches that to prepare breads and the like from amaranth composite flours requires as essential ingredients in addition to amaranth and wheat flours: sugar, fat, milk, malt, chemical modifiers, and the like.

In working with amaranth flours, I began by separating coarse and fine flour fractions from the coarse whole amaranth flour as described in the art. When the various fractions were used as the sole flour in baked products, milk substitutes, and the like, heavy, crumbly, and largely undesirable products were produced. To achieve the texture, cohesiveness, and desired risen structure of products produced from an amaranth flour, a fine, whole amaranth flour was needed.

Such a flour, the flour of the instantly claimed invention, was milled in a stone mill set at the finest setting possible and the meal was passed in small amounts through the mill, with repetitions as necessary to produce a finely comminuted flour. However the flour can be prepared by any techniques necessary to achieve the desired result, provided that mechanical flour fraction separation processes are minimized.

With this flour the applicant was able to develop processes appropriate to the production of many previously unavailable products. The new amaranth flour, together with only water, oil, and leavening, is used to make breads, cookies, pastas, and the like. There are no teachings regarding the use of amaranth flour to prepare milk substitutes, egg substitutes, or substitutes for nut butters. There is no teaching to suggest that such uses are possible.

Based on the information available and based on the teachings of the art, an investigator with average skill in the art would have no reason to suspect the surprising improvements in quality and characteristics of the instantly claimed amaranth flour.

It has now been found that flours having finer, more uniform particle size can be prepared that produce greatly improved products including those where amaranth flour is the primary or only ingredient other than water and oil.

Lotus: Lotus was investigated as a source for new food products. Lotus is an aquatic plant which is virtually completely edible. The lotus produces tuberous roots which are commonly eaten in the Orient as side dishes and in combination with many other ingredients. Lotus starch exists in commerce with typical uses of starch. Prior to the present invention a whole flour of lotus was unknown.

In my early research on developing lotus flour, the lotus flour was made by a high speed impact method which produced a flour of wide particle-size distribution, with the fibrous portions of the tuber remaining in the larger particle sizes, and rendering the flour unsuitably heavy and gritty. When screened, (as is accepted practice in the art to obtain a fine flour) the large particles were removed; this produced a lighter and less gritty flour, but one poorly suited for producing breads and other products where consistency and lightness are important.

I then developed a new process for preparing lotus flour which involved incorporating more fibrous and non-farinaceous material into the flour, and obtaining a more uniform particle size distribution in the flour. This flour, the flour of the instantly claimed invention, is suitable for use in baked and other products, and it was possible to develop new processes, different from conventions of the art, for using the lotus flour of the instantly claimed invention to prepare products with properties and characteristics previously only obtainable from products containing wheat and other grains, legumes, eggs, milk, nuts and the like.

SUMMARY OF THE PREFERRED EMBODIMENTS

It is one object of the present invention to provide flours and advantageous processes for producing flours from the camote or boniato and all other light-fleshed tuberous varieties in the family Convolvulaceae. Throughout this application, the words ,camote and ,boniato, will refer to the dark or light red or purple skinned varieties of the white or creamy fleshed sweet potato.

Similarly, it is one object of the present invention to provide flours and advantageous processes for producing flours from: 1) the tubers of the cassava and all other plants producing edible tubers or tuberous roots of the family Euphorbiaceae: 2) tubers of malanga and all plants producing tubers of the family Araceae; 3) the seeds of the amaranth quinoa and all other seeds from the families Chenopodiaceae and Amaranthaceae, 4) the tubers of the yam and all plants producing tubers in the family Dioscoreaceae: and 5) the tubers of the lotus, arrowhead, buckbean and all other plants producing tubers in the families Nymphaeaceae, Alismataceae, and Gentianaceae.

Throughout this section, 'Summary of the Preferred Embodiments', the terms 'flour' or 'flours' will refer to the flours of the above referenced seeds or tubers—namely flours of white sweet potato, cassava, malanga, amaranth, yam, lotus, arrowhead, and buckbean, and flours from other varieties in closely related families—prepared by the processes of the instantly claimed invention.

Another object of the present invention to provide advantageous processes of producing valuable edible products from the flours.

Another object of the present invention is to provide edible compositions of matter from the flour.

Another object of the present invention is to provide advantageous processes for producing substitutes for milk, milk-products, and milk containing products.

Still another object of the present invention is to provide advantageous processes for producing substitutes for products containing eggs.

Still another object of the present invention is to provide advantageous processes for producing substitutes for legumes and legume-containing products.

Another object of the present invention is to provide advantageous processes for producing substitutes for nut butter products and products containing nut butters.

Another object of the present invention is to provide advantageous processes for producing substitutes for wheat, other grains, legumes, eggs, milk, and yeast-containing products using the above referenced flours as essentially the only ingredient.

Still another object of the present invention is to provide novel and advantageous processes for producing the following products with the above referenced flours as the only ingredient other than ingredients selected from: water, oil, salt, and leavening agent: pastas, cereals, pancakes, bread, cakes, creamed cereals, cereal shreds, imitation nut butters, imitation mayonnaise, mashed potato substitutes, breads, bread crumbs. croutons, cookies, crackers, tortillas, chips, puffed chip-like products, cornbread, pie crust, pizza dough, dough-wrapped products, doughnuts, dumplings, hush puppies, pretzels, batter, milk, ice cream, milk shake, puddings, custards, light and heavy creams, condensed milk, muffins, waffles, french toast, crepes, sweet potato pie, and dry mixes for many products.

Another object of the present invention is to provide novel and advantageous processes for producing the following products with the above referenced flours as a primary ingredient: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, cornbread, pie crust, pizza dough, dough-wrapped products, doughnuts, dumplings, hush puppies, pretzels, batter, milk, ice cream, milk shake, puddings, custards, light and heavy creams, condensed milk, muffins, waffles, french toast, protein coating batter, crepes, sweet potato pie, and dry mixes for many products.

Another object of the present invention is to provide advantageous processes for producing infant formulas.

Another object of the present invention is to provide advantageous processes for producing pharmaceutical products that are more effective for allergy patients by the use of hypoallergenic flours such as the above referenced flours as inert ingredients.

Another object of the present invention is to provide advantageous processes for producing cosmetics containing the above referenced flours as cosmetic base and facial powder, and other uses.

Briefly, these objects and other objects of the present invention as hereinafter will become more readily apparent can be attained by a plurality of method embodiments which employ the above referenced flours to prepare a variety of different foodstuffs.

DETAILED DESCRIPTION OF THE PREFERRED EMBODIMENTS

Camote, boniato, and all sweet potatoes and other tubers with light colored flesh of family Convolvulaceae: The words white sweet potato as used in this application are intended to include all tubers with light colored flesh of the family Convolvulaceae.

It has now been found that a flour from white sweet potatoes that is useful in the production of many food products can be made. Moreover the flour can be used in every way wheat flour is used, although the processes are totally different.

Because sweet potatoes are frequently well-tolerated by people with multiple food allergies, and would be a highly nutritious, hypoallergenic food stuff, the applicant carefully investigated sweet potatoes and found one variety of white sweet potato, the camote or boniato, whose properties seemed to be significantly different from the others. This sweet potato is about equal in length to the orange varieties, but is 3-4 times greater in diameter. The outside flesh is reddish-purple and tough. The inside flesh is creamy white and very hard. Although it tastes like a sweet potato, after cooking the flesh does not fall apart as the orange varieties do. This variety is not well known in the US where it is used primarily by people from Central and South America in the traditional ways of their homelands. In these countries the fresh tuber is used in almost any way a fresh orange sweet potato or white potato is used—baked, fried, boiled, mashed. The camote are also processed for the starch which is used as a thickener.

In my previous attempts to prepare flour of the desired properties, white sweet potato flour was made by soaking white sweet potato tubers in water between the peeling and drying steps, it has now been found that the soaking step can be eliminated thus eliminating spoilage problems during drying steps and producing a flour of lower moisture content. Furthermore the applicant has found that eliminating a high impact grinding method, produced a more uniformly fine flour which incorporates a greater proportion of the plant fiber into the flour, thus greatly improving the ability of the doughs to hold a rise and produce consistently uniform products.

In the preferred embodiment, white sweet potatoes are subjected to any preprocessing steps of washing, scrubbing, cutting, rinsing and the like, peeled by any techniques of the art, peeling while clean (not recycled) water is passing over the tubers is preferred although white sweet potatoes may also be processed unpeeled and with or without simultaneous washing and peeling, rinsing (in distilled water is preferred although may be omitted), comminuting, slicing, chopping or any other technique desired (although not necessary). preferably shredding; dehydrating the material by air drying (at any appropriate temperature), freeze drying, vacuum drying or any other technique or combination of techniques of the art, preferably air drying, and comminuting by such techniques as to produce a moderately fine to fine flour (with a moisture content of less than 15%, preferably 2-5%) that incorporates 20% or more of the plant fiber, preferably uses 100% of the fibers, in other words, incorporates the entire tuber into the flour or other products produced. Although moderately fine or fine flours are desired, coarseness or fineness of the product is not critically important in some products.

Specifically, comminute shreds to produce a flour of relatively uniform particle size, with a particle size selected from: coarse meal, moderately fine flour or powder (in which entire flour passes through a 0.015 in screen), fine flour or powder, or very fine powder. Fine or very fine flours are preferred (except where a coarse flour is indicated by use). More preferred flour particle size is no greater than 0.005 inch mesh. Most preferred particle size range is up to one in which entire flour produced passes through a screen of 0.001 inch mesh.

In pulverizing and comminuting steps, desired particle size is achieved while retaining most or all of the plant fiber and other non-farinaceous substance of the tuber. Preferably the flour product contains at least 75% of the plant fiber and other non-farinaceous substance of the tuber, more preferably the flour product contains at least 90% of the plant fiber and other non-farinaceous substance of the tuber, most preferably the flour product contains substantially all of the plant fiber and other non-farinaceous substance of the tuber.

Dry raw white sweet potatoes may be processed to flour material. Thus, in one flour embodiment, dried peeled or unpeeled tubers are preferably peeled, comminuted to a moderately fine to fine powder by any conventional means, preferably a particle size of 0.015 inch and less, although the coarseness or fineness of the flour is not critical in some processes and products.

In yet another embodiment the above process is repeated with the added step of partial or complete cooking of the white sweet potato by steam heating, boiling, baking or any other desired means, steam heating is preferred, either severally, prior to, or in combination with, drying steps or any other step or steps in the process to produce a cooked or partially cooked flour product.

In the work with white sweet potato flour I began product development by following recipes for wheat flour, and making substitutions according to standard formulas given in allergy cookbooks for egg and milk replacers. The result was resound failures. For example, the bread rose nicely, only to fall flat, and had a $\frac{1}{4}$ to $1\frac{1}{2}$ inch gummy layer on the bottom, the early loaves of bread were about $2\frac{3}{4}$ inches high along the sides and $1\frac{1}{2}$ inches high in the center. Wheat-based processes could not be readily adapted for use with the new flour; they were abandoned, and new processes not heretofore known were developed.

Cassava tubers and all other edible tubers of the family Euphorbiaceae:

The word cassava as used in this patent application is intended to include cassava and all other tubers of the family Euphorbiaceae.

It has now been found that flour from cassava can be used in the production of many food products. Moreover the flour can be used in every way wheat flour is used, although the processes are totally different.

In my previous attempts to prepare flour of the desired properties, cassava flour was made by soaking cassava tubers in water between the peeling and drying steps. It has now been found that the soaking step can be eliminated thus eliminating spoilage problems during drying steps and producing a flour of lower moisture content. Furthermore, the applicant has found that eliminating a high impact grinding method, produced a more uniformly fine flour which incorporates a greater proportion of the plant fiber into the flour, thus greatly improving the ability of the doughs to hold a rise and produce consistently uniform products.

In a preferred embodiment, cassava and other tubers are subjected to any preprocessing steps of washing, scrubbing, culling, rinsing and the like, peeled by any techniques of the art, peeling while clean (not recycled) water is passing over the tubers is preferred although cassava may also be processed unpeeled, rinsing (in distilled water is preferred although may be omitted), comminuting, slicing, chopping or any other techniques desired (although not necessary), preferably shredding; dehydrating the material by air drying (at any appropriate temperature), freeze drying, vacuum drying or any other techniques or combination of techniques of the art, preferably air drying, and comminuting by such techniques as to produce a flour with a moisture content of less than 15%, preferably 2-5%, that incorporates 20% or more of the plant fiber, preferably uses 100% of the fibers, in other words, incorporates the entire tuber into the flour or other products produced.

Specifically, comminute shreds to produce a flour of relatively uniform particle size, with a particle size selected from: coarse meal moderately fine flour or powder (in which entire flour passes through a 0.015 in screen), fine flour or powder, or very fine powder. Fine or very fine flours are preferred (except where a coarse flour is indicated by use). More preferred flour particle size is no greater than 0.005 inch mesh. Most preferred particle size range is one in which entire flour produced passes through a screen of 0.001 inch mesh.

In comminuting and comminuting steps, desired particle size is achieved while retaining most or all of the plant fiber and other non-farinaceous substance of the tuber. Preferably the flour product contains at least 50% of the plant fiber and other non-farinaceous substance of the tuber (which is defined to include woody ends, inner portions of the peel, and other woody portions that are not incorporated into cassava flour), more preferably the flour product contains at least 75% of the plant fiber and other non-farinaceous substance of the tuber, more preferably the flour product contains at least 90% of the plant fiber and other non-farinaceous substance of the tuber, most preferably the flour product contains substantially all of the plant fiber and other non-farinaceous substance of the tuber.

Dry raw cassava may be processed to flour material. Thus, in one flour embodiment, dried peeled or unpeeled tubers are preferably peeled, comminuted to a moderately fine to fine powder by any conventional means, preferably a particle size of 0.015 inch and less, although the coarseness or fineness of the flour is not critical in some processes and products.

In another embodiment, a cooked flour may be produced in the method above with the added step of heating by any means available to the art in processes prior to, during, or after and in any combination with the processes listed above.

In the work with cassava, I began product development by following recipes for wheat flour, and making substitutions according to standard formulas given in allergy cookbooks for egg and milk replacers. The result was resound failures. Wheat-based processes could not be readily adapted for use with the new flour; they were abandoned, and new processes not heretofore known were developed.

Malanga and other edible aroids: The word malanga as used in this patent application is intended to include malanga, taro, amorphophallus and all other tubers of the family Araceae.

It has now been found that flour from malanga can be used in the production of many food products. Moreover the flour can be used in every way wheat flour is used, although the processes are totally different.

Because malanga are frequently well-tolerated by people with multiple food allergies, and would be a highly nutritious, hypoallergenic food stuff, I carefully investigated malanga and found that malanga, and other tubers of family Araceae are well suited to multiple food products. The malanga is similar in size and shape to a white Russet potato, often being slightly smaller in girth. The inside flesh is crisp but oozes a sticky latex like fluid, the flesh is generally white but may also be yellow, pink, or violet. The outer skin is hairy and bulb-like in appearance. The malanga in taste and texture after cooking is very similar to a white potato, but when cooling after heat treatment and gelatinization, the malanga becomes more firm. The malanga and taro are not well known in the U.S., except for its use in making poi, but it is appearing in produce departments of gourmet food stores where it is sold as a potato substitute. In tropical countries throughout the world, malanga, taro, etc are well known as yautia, cocoyam, eddo, coco, tannia, and sato imo. Common uses include: fu-fu, a very heavy paste eaten with soups and stews; poi; gravies and sauces from the starch; and heavy, taro breads where mashed vegetable paste is added to wheat and egg based dough mixtures.

In my previous attempts to prepare flour of the desired properties, malanga flour was made by soaking malanga tubers in water between the peeling and drying steps, it has now been found that the soaking step can be eliminated thus eliminating spoilage problems during drying steps and producing a flour of lower moisture content. Furthermore the applicant has found that eliminating a high impact grinding method, produced a more uniformly fine flour which incorporates a greater proportion of the plant fiber into the flour, thus greatly improving the ability of the doughs to hold a rise and produce consistently uniform products.

In the preferred embodiment malanga and other tubers are subjected to any preprocessing steps of washing, scrubbing, cutting, rinsing and the like, peeled by any techniques of the art, peeling while clean (not recycled) water in passing over the tubers is preferred although malanga may also be processed unpeeled, rinsing (in distilled water is preferred although may be omitted), comminuting, slicing, chopping or any other technique desired (although not necessary) preferably shredding; dehydrating the material by air drying (at any appropriate temperature), freeze drying, vacuum drying or any other technique or combination of techniques of the art, preferably air drying, and comminuting by such techniques as to produce a flour (with a moisture content of less than 15%, preferably 2-5%) that incorporates 20% or more of the plant fiber, preferably uses 100% of the fibers, in other words, incorporates the entire tuber into the flour or other products produced.

Specifically, comminute shreds to produce a flour of relatively uniform particle size, with a particle size selected from: coarse meal, moderately fine flour or powder (in which entire flour passes through a 0.015 in screen), fine flour or powder, or very fine powder. Fine or very fine flours are preferred (except where a coarse flour is indicated by use). More preferred flour particle size is no greater than 0.005 inch mesh. Most preferred particle size range is one in which entire flour produced passes through a screen of 0.001 inch mesh.

In pulverizing and comminuting steps, desired particle size is achieved while retaining most or all of the plant fiber and other non-farinaceous substance of the tuber. Preferably the flour product contains at least 75% of the plant fiber and other non-farinaceous substance of the tuber, more preferably the flour product contains at least 90% of the plant fiber and other non-farinaceous substance of the tuber, most preferably the flour product contains substantially all of the plant fiber and other non-farinaceous substance of the tuber.

Dry raw malanga may be processed to flour material. Thus, in one flour embodiment, dried peeled or unpeeled tubers are preferably peeled, comminuted to a moderately fine to fine powder by any conventional means, preferably a particle size of 0.015 inch and less, although the coarseness or fineness of the flour is not critical in some processes and products.

In another embodiment, a partially or completely cooked flour may be produced in the method above with the added step of heating by any means available to the art in processes prior to, during, or after and in any combination with the processes listed above.

In the work with malanga, I began product development by following recipes for wheat flour, and making substitutions according to standard formulas given in allergy cookbooks for egg and milk replacers. The result was resound failures. Wheat-based processes could not be readily adapted for use with the new flour; they were abandoned, and new processes not heretofore known were developed.

Tropical yams and other tubers of family Dioscoreaceae: The word "yam" as used in this patent application is intended to include the name and cush-cush, and all other tubers in the family Dioscoreaceae.

It has now been found that flour from yams and other tuberous plants in the family, Dioscoreaceae can be used in the production of many food products.

The yam also called name, cush-cush, and mapuey and so forth is a tuber that varies in size from smaller than a potato to 100 pounds and more. Several varieties include black, yellow and white. The outside skin may be reddish-brown, brown, grey, or black and so forth. This variety is not well known in the U.S. where it is used primarily by people from Central and South America in the traditional ways of their homelands. In these countries the fresh tuber is used in almost any way a white potato is used—baked, fried (but will be very strongly flavored or bitter), boiled, mashed. The yam also has been processed for the starch which is used as a thickener.

In the first embodiment, a pleasantly mild-flavored and non-bitter flour or flour-like substance is made from tropical yams in processes involving optional peeling by any conventional means, optional rinsing, trimming, optional cooking steps, optional shredding or otherwise comminuting to any desired size, and then drying by any means that avoids introducing a strong flavor or bitter taste into the flour such as air drying, freeze drying, vacuum drying, and the like, preferably drying at temperatures less than 50° F., more preferably drying at temperatures less than 32° F. and comminuting the dried products under any conditions that would not heat or otherwise change the particles sufficiently to introduce a strong flavor or bitter taste into the flour. These steps may be taken in any desired combination, in any desired order, including simultaneously.

Preferably, the tubers are peeled and trimmed to remove spots, worm holes, moldy or spotted sections and the like, while being held under running water, rinsed in distilled water, cut into cubes of any size, preferably 2×2×2, and subjected to heat with steam until thoroughly gelatinized. The tubers are then trimmed to remove all black, grey or otherwise discolored sections, and dried by a low temperature drying method such as freeze-drying. The dried product is then comminuted to a flour of various particle size distribution in a low temperature grinding process, in one method the dried flour is frozen and comminuted while still very cold and with short bursts of power to avoid the bitter taste.

In another preferred embodiment, the tubers are peeled as described above and then comminuted to any desired size, dried by freeze-drying or other vacuum drying methods, comminuted to flour of various particle sizes by any method that does not raise the temperature of the flour or otherwise alter it sufficiently to introduce a strong flavor or bitter taste.

Specifically, comminute shreds to produce a flour of relatively uniform particle size, with a particle size selected from: coarse meal, moderately fine flour or powder (in which entire flour passes through a 0.015 in screen), fine flour or powder, or very fine powder. Fine or very fine flours are preferred (except where a coarse flour is indicated by use); more preferred flour particle size is no greater than 0.005 inch mesh. Most preferred particle size range is one in which entire flour produced passes through a screen of 0.001 inch mesh.

In pulverizing and comminuting steps, desired particle size is achieved while retaining most or all of the plant fiber and other non-farinaceous substance of the tuber. Preferably the flour product contains at least 75% of the plant fiber and other non-farinaceous substance of the tuber, more preferably the flour product contains at least 90% of the plant fiber and other non-farinaceous substance of the tuber, most preferably the flour product contains substantially all of the plant fiber and other non-farinaceous substance of the tuber.

Dry raw yams may be processed to flour material. Thus, in one flour embodiment, dried peeled or unpeeled tubers are preferably peeled, comminuted to a moderately fine to fine powder by any conventional means, preferably a particle size of 0.015 inch and less, although the coarseness or fineness of the flour is not critical in some processes and products.

In the work with yams, I began product development by following recipes for wheat flour, and making substitutions according to standard formulas given in allergy cookbooks for egg and milk replacers. The result was resound failures. Wheat-based processes could not be readily adapted for use with the new flour; they were abandoned, and new processes not heretofore known were developed.

Amaranth, quinoa and other seeds of families Amaranthaceae and Chenopodiaceae: The word amaranth as used in this patent application is intended to include amaranth, quinoa and all other seeds of the Chenopodiaceae and Amaranthaceae families.

It has now been found that flour from amaranth can be used in the production of many food products. Moreover the flour can be used in every way wheat flour is used, although the processes are totally different.

Amaranth is a domesticated plant that is directly descended from the pigweed. Many species and varieties exist throughout the world. Amaranth seeds and meal-type flour are used in wide numbers of products, which rely on other flours and the like to produce acceptable products. Amaranth is essentially not mentioned in the patent literature.

Quinoa seeds are about twice the size of amaranth seeds, and are primarily used as a cereal product.

Products of amaranth flour that are presently available are coarse, heavy, and grainy, because the amaranth seeds are very hard. The applicant has found that prolonged or repeated grinding cycles, are sufficient to produce a uniformly fine flour that can be used to produce greatly improved products including many products those in which amaranth is the primary or only ingredient.

In the preferred embodiment, amaranth seeds are pulverized, communited and the like by any desired technique or combination of techniques common to the art to produce a meal. The particle sizes are further reduced to a moderate to fine flour by repeated steps of comminuting, grinding, comminuting, smashing, and the like, in any combination together with optional drying by any conventional method, in as many repetitions as are needed to produce a relatively uniform flour of moderate to fine particle size with 10–100% preferably all components of the seed remaining in the flour.

Specifically, comminute seeds to produce a flour of relatively uniform particle size, with a particle size selected from: coarse meal, moderately fine flour or powder (in which entire flour passes through a 0.015 in screen), fine flour or powder, or very fine flour. Fine or very fine flours are preferred (except where a coarse flour is indicated by use). More preferred flour particle size is no greater than 0.005 inch mesh. Most preferred particle size range is one in which entire flour produced passes through a screen of 0.001 inch mesh.

In pulverizing and comminuting steps, desired particle size is achieved while retaining most or all of the plant fiber and other non-farinaceous substance of the tuber. Preferably the flour product contains at least 50% of the plant fiber and other non-farinaceous substance; more preferably, the flour product contains at least 75% of the plant fiber and other non-farinaceous substance: more preferably the flour product contains at least 90% of the plant fiber and other non-farinaceous substance, most preferably the flour product contains substantially all of the plant fiber and other non-farinaceous substance.

Dry raw amaranth may be processed to flour material. Thus, in one flour embodiment, amaranth seeds are preferably peeled, comminuted to a moderately fine to fine powder by any conventional means, preferably a particle size of 0.015 inch and less, although the coarseness or fineness of the flour is not critical in some processes and products.

In another flour embodiment amaranth seed, meal or flour is combined with water in proportions of from 1:3 to 1:200, preferably 1:10 in any desired way and heated by any conventional means including, steam Jackets and pressure, and the like under temperatures, pressure, and length of time for heating to an appropriate for the processes used, and as necessary to form a soft, gelatinized mass or mixture varying in consistency from thick paste to water. Either prior to, during heating, or after heating, the mass is subjected to methods of pureeing, pulping, blending, comminuting, pulverizing and the like to form a smooth, homogeneous fluid or paste. This mixture is dried by suitable means of the art and comminuted to flakes or a fine or coarse powder.

In another embodiment, a flour may be produced in the manner of the first flour embodiment, with the added step of toasting the amaranth during or before grinding.

In yet another embodiment a flour may be produced in the manner of the first embodiment, with the added step of popping the amaranth seeds before grinding or otherwise comminuting.

In the work with amaranth, I began product development by following recipes for wheat flour, and making substitutions according to standard formulas given in allergy cookbooks for egg and milk replacers. The result was resound failures. Wheat-based processes could not be readily adapted for use with the new flour; they were abandoned, and new processes not heretofore known were developed.

Lotus, arrowhead, and buckbean and other edible tubers from families Nymphaceae, Alismataceae, and Gentianaceae: The word "lotus" as used in this patent application is intended to include tuberous roots of lotus, arrowhead and buckbean and all other plants of the families Nymphaeaceae, Alismataceae, and Gentianaceae.

It has now been found that flour from lotus can be used in the production of many food products. Moreover the flour can be used in every way wheat flour is used, although the processes are totally different.

In my previous attempts to prepare flour of the desired properties, lotus flour was made by soaking lotus tubers in water between the peeling and drying steps, it has now been found that the soaking step can be eliminated thus eliminating spoilage problems during drying steps and producing a flour of lower moisture content. Furthermore the applicant has found that eliminating a high impact grinding method, produced a more uniformly fine flour which incorporates a greater proportion of the plant fiber into the flour, thus greatly improving the ability of the doughs to hold a rise and produce consistently uniform products.

In the preferred embodiment, lotus are subjected to any preprocessing steps of washing, scrubbing, cutting, rinsing and the like, peeled by any techniques of the art, peeling while Clean (not recycled) water is passing over the tubers is preferred although lotus may also be processed unpeeled and with or without simultaneous washing and peeling, rinsing (in distilled water is preferred although may be omitted), comminuting, slicing, chopping or any other technique desired (although not necessary), preferably shredding; dehydrating the material by air drying (at any appropriate temperature). freeze drying, vacuum drying or any other technique or combination of techniques of the art, preferably air drying, and comminuting by such techniques as to produce a moderately fine to fine flour (with a moisture content of less than 15%, preferably 2–5%) that incorporates 20% or more of the plant fiber, preferably uses 100% of the fibers, in other words, incorporates the entire tuber into the flour or other products produced. Although moderately fine or fine flours are desired, coarseness or fineness of the product is not critically important in most products.

In another embodiment, a partial or complete cooked flour may be produced in the method above with the added step of heating by any means available to the art in process prior to, during, or after and in any combination with the processes listed above.

Specifically, comminute shreds to produce a flour of relatively uniform particle size, with a particle size selected from: coarse meal, moderately fine flour or powder (in which entire flour passes through a 0.015 in screen), fine flour or powder, or very fine powder. Fine or very fine flours are preferred (except where a coarse flour is indicated by use). More preferred flour particle size is no greater than 0.005 inch mesh. Most preferred particle size range is one in which entire flour produced passes through a screen of 0.001 inch mesh.

In pulverizing and comminuting steps, desired particle size is achieved while retaining most or all of the plant fiber and other non-farinaceous substance of the tuber. Preferably the flour product contains at least 75% of the plant fiber and other non-farinaceous substance of the tuber, more preferably the flour product contains at least 90% of the plant fiber and other non-farinaceous substance of the tuber, most preferably the flour product contains substantially all of the plant fiber and other non-farinaceous substance of the tuber.

Dry raw lotus may be processed to flour material. Thus, in one flour embodiment, dried peeled or unpeeled tubers are preferably peeled, comminuted to a moderately fine to fine powder by any conventional means, preferably a particle size of 0.015 inch and less, although the coarseness or fineness of the flour is not critical in some processes and products.

In the work with lotus, I began product development by following recipes for wheat flour, and making substitutions according to standard formulas given in allergy cookbooks for egg and milk replacers. Wheat-based processes could not be readily adapted for use with the new flour; they were abandoned, and new processes not heretofore known were developed.

A cereal substance or constituent of cereal may be prepared from the dried shreds of the lotus tuber, which shreds optimally may be roasted by any desired conventional technique.

A particulate material which is useful as a cereal substitute for the likes of cream of wheat can be prepared by comminuting dried lotus tubers to particle sizes ranging from 0.3 inch to 0.02 inch, preferably 0.06 inch. The tuber may be peeled or unpeeled before processing; peeled tubers are preferred.

Detailed Description of Preferred Embodiments of Processes for Using the Instantly Claimed Flours: The above flours may be used in many processes to produce desirable products. Detailed descriptions of preferred embodiments for white sweet potatoes are presented below. Each description of white sweet potato embodiments is followed by descriptions of any differences in the corresponding embodiments for the other flours. All of the following ratios ar by weight unless otherwise noted.

Throughout this specification, the terms 'leavening agent' or 'conventional leavening agents' are intended to refer to conventional baking powders, and also to include leavening agents that would be specifically appropriate for hypoallergenic uses in which a flour of the present invention replaces more standard flours of corn starch and potato starch which generally act as inert ingredients in commercial baking powders, such as white sweet potato baking powder. Any reference to specific baking powders such as white sweet potato baking powder is also intended to refer to any other specific baking powder and to conventional baking powders. Baking sodas, cream of tartar, other chemical leavening agents conventional to the art, and yeast-type leavening agents can also be used in the processes described below.

A cereal substance or constituent of cereal may be prepared from the dried shreds or particles of any shape of the white sweet potato tuber, which are roasted, baked, toasted (with or without oil) by any desired conventional technique. Similarly, cassava, malanga, yam, and lotus shreds optimally be roasted by any desired conventional technique.

A particulate material which is useful as a cereal substitute for the likes of cream of wheat can be prepared by comminuting dried white sweet potato tubers to particle sizes ranging from 0.3 inch to 0.02 inch, preferably 0.06 inch. The tuber may be peeled or unpeeled before processing; peeled tubers are preferred. A similar product can be made as described above using cassava, malanga, yam, and lotus.

A bread product can be prepared from white sweet potato flour, water, and a small amount of salt (optional), oil (optional), and any conventional leavening agent in proportions ranging from 1:$\frac{1}{2}$ to 1:4, by weight, of flour and water, preferably 1:1.4 in processes of mixing at any desired speed, preferably a moderately high speed, shaping, and baking in any desired order or combinations of techniques common to the art. The white sweet potato bread is baked at temperatures ranging from 275–550° F., preferably 425° F., for 15–90 minutes, preferably 50 minutes. Processes are as described above for other flours, with exceptions as noted. For cassava flour, ranges are 1:$\frac{1}{4}$ to 1:4, preferably 1:0.9. For malanga flour the preferred proportion is 1:1$\frac{1}{4}$; preferred baking time is 40 minutes. For yam flour, the preferred ratio is 1:1.4. For amaranth flour the range is 1:0.1:0 to 1:4:1 preferably 1:0.4:0.2 for flour, water and oil. For lotus flour the preferred ratio is 1:1.5, preferred baking time is 60 minutes at 400° F.

In still another embodiment the bread products described above, and products such as cornbread, cookies, pancakes, muffins, and the like described in examples which follow may be used to prepare bread crumb and crouton-type and other similar products. Breads and the other products, in processes including but not limited to various orders and combinations of drying, toasting, coating, cutting, slicing, comminuting, and the like in steps conventional to the art may be used to produce bread crumb products with all possible uses of any other bread crumb products. These uses include but are not limited to: coating mixes for use alone or with batters, salad toppings, pie crusts, stuffings, and the like.

By techniques in any desired order or combination of slicing, drying, roasting, toasting, baking, and the like, cubed products called croutons may be produced. These may be used on salads, soups, stews, stuffings, and any other ways croutons are used.

In another embodiment, a cornbread-like product can be prepared from white sweet potato flour, water, oil, and small amounts of salt (optional), sweeteners (optional), and any conventional leavening agent in proportions of flour, water and oil ranging from 1:6:$\frac{1}{4}$ to 1:1/2:0, by weight, preferably 1:1.5:1/24 with processes of mixing at any desired speed, preferably a moderately high speed, shaping, and baking in any desired order or combinations of techniques common to the art. The white sweet potato cornbread is baked at temperatures ranging from 275–550° F., preferably 425° F., for 15–90 minutes, preferably 50 minutes. When a liquid sweetener such as a honey is used, the proportions range from 1:6:2:$\frac{1}{4}$ to 1:$\frac{1}{4}$:0:0, preferably 1:1.2:0.2:0.04 of white sweet potato flour, water, honey, and oil.

Processes for preparing a cornbread-like product are as described above for yam flour, exceptions for other flours are as noted. For cassava flour the preferred ratio is 1:1.2:0.1. When a liquid sweetener is used the preferred ratio of cassava flour, water, honey, and oil is 1:1.2:0.2:1/10. For malanga flour the range is 1:$\frac{1}{4}$ to 1:4, preferably 1:1$\frac{1}{4}$ for flour and water. If liquid sweetener is used the proportions range from 1:6:2 to 1:0.5:0, preferably 1:1.25:0.4 for malanga flour, water, and honey. The preferred baking time is 40 minutes. For amaranth flour the range is 1:10:0 to 1:4:1, preferably 1:0.4:0.2; when a liquid sweetener is added the proportions range from 1:6:2:$\frac{1}{4}$ to 1:0.1:0:0, preferably 1:0.4:0.3:0.2 of amaranth flour. water, honey and oil. For lotus, the preferred baking time is 30–40 minutes, and the preferred ratio for liquid sweetener is 1:1.2:1/20:1/25 for flour, water, honey and oil.

In another embodiment, a cake dough product can be prepared, in the method described above for cornbread by increasing ranges and preferred amounts: the amount of oil by 100%, increasing the amount of honey by 20%, and increasing the amount of baking powder by 25–50%. Alternatively, honey may be omitted. These doughs produce a baked cake-like product without added ingredients, although ingredients commonly used in the art may also be incorporated into the dough or added to the finished products. Similar modifications can be used to prepare cake dough products for cassava, malanga, yam, amaranth, and lotus flours.

In still another embodiment by the processes described for cornbread products, muffins may be produced. The range of ratios of flour, water, and oil are the same as for the cornbread product, with preferred proportions of 1:1.3:1/24. Processes are as described above for cassava and yam flours, with exceptions as noted for other flours. For malanga flour the range is 1:½ to 1:4. preferably 1:1¼ for flour and water. For amaranth flour the preferred ratio is 1:0.4:0.2. For lotus flour the preferred ratio is 1:1.5:1/24.

In another embodiment, products the likes of pancakes, doughnuts, hush puppies, batter, crepes, dumplings and waffles can be prepared from combinations of white sweet potato flour, water, oil, and small amounts of salt (optional). sweeteners (optional), and of any conventional leavening agents in proportions virtually identical to those for cornbread. The ranges of general proportions are identical with preferred proportions being 1:1.5:1/12. These products are mixed, molded, shaped, fried, and so forth as appropriate for the product.

Processes are as described above for other flours, with exceptions as noted. For cassava flour, the preferred ratio is 1:1.2:0.13. For malanga flour, the preferred ratio is 1:1.3:1/7. For uncooked yam flour, the preferred ratio is 1:1.5:1/24. For cooked yam flour, proportions of frozen flour, boiling water and oil range from 1:6:1 to 1:½:0, preferably 1:2.7:1/5. For amaranth flour the range is 1:¼:0 to 1:2:½, preferably 1:1 1/4:1/6. For lotus flour the preferred ratio is 1:1.5:1/12.

In still another embodiment the above described pancake batters prepared as described earlier may be used as a pizza dough. In processes involving pouring the batter onto an appropriately shaped or sufficiently large surface, heating or baking in temperatures ranging from 375–525° F. preferably 425° F., until dough is almost done but still tacky on the top, about 10–30 minutes, preferably. Add any desired ingredients including but not limited to various meats, cheeses, vegetables, spices, and other materials common to the art. Although any ingredients may be used, hypoallergenic ingredients might include ground precooked venison and nopales. Bake until dough is completely done and ingredients thoroughly cooked, about 6–20 minutes. Alternatively, the toppings described above may be placed on the batter before cooking begins. Alternatively, the above dough may be thoroughly baked, toppings added, and pizza reheated. The same process can be used for cassava, malanga, yam, amaranth and lotus batters.

Alternatively the dough described for pie crust may be used as a pizza dough. The dough is prepared as described in the example, the dough is rolled out to the desired length, width, and thickness, toppings of any kind are added and the mixture is baked at 350° F. for 10–30 minutes. Pie crusts of cassava, malanga, yam, amaranth, and lotus flours can be used similarly.

In yet another embodiment, a product such as dumplings can be prepared from combinations of white sweet potato flour, water, oil and a small amount of salt (optional). and any conventional leavening agent in proportions identical to those described previously for pancake batter. The ingredients are combined and the batter is then cooked as follows. Teaspoon sized portions of batter are dropped into rapidly boiling thickened water for 2–6 minutes, preferably 5 minutes. Similarly, dumplings can be prepared from batters of cassava, malanga, yam, and lotus flours with ratios and preferred proportions of ingredients as described earlier for pancake batter.

In yet another embodiment, a product such as waffles can be prepared from white sweet potato flour, water, oil, and small amounts of salt (optional), sweeteners (optional). and any conventional leavening agent. Ranges and preferred proportions are the same as those described previously for pancake batter. Processes of combining ingredients and batter preparation are as described for pancake batter. Batter is then placed in waffle irons or other type of molds and heated by conventional means. Similarly, waffles can be prepared from batters of cassava, malanga, yam and lotus flours with ratios and preferred proportions of ingredients as described earlier for pancake batter. For amaranth flour the range is 4:1:¼ to ½:1:0 preferably 1.6:1:0.15.

In another embodiment, a product such as french toast batter can be prepared from white sweet potato flour, water, oil, uncooked, proteinaceous material, and a small amount of salt (optional) in proportions ranging from 5:12:8:8 to 1/10:12:O:O by weight, preferably 1:12:2:2. in processes of gelatinizing the flour and water mixture, combining with remaining ingredients and blending with high speed blending equipment until smooth and homogenous. Material to be coated and prepared for french toast is preferably white sweet potato bread, although any other bread or bread-like product may be used, and cooking is by any accepted technique. Alternatively batter may be prepared by the method above omitting the step of gelatinizing the flour-water mixture. Alternatively, the proteinaceous material may be omitted, with the above proportions of flour and water remaining unchanged. The batter may be used alone, or in combination with bread crumbs and any other coating materials. Processes are as described above for other flours, with exceptions as noted. For cassava flour the range is 1:100:15:8 to 1:2:0:0, preferably 1:16:5.6:2. For malanga flour the range is 5:14:8:8 to 0.1:12:0:0, preferably 1:14:2.4:2. For yam flour the range is 5:12:8 to 0.1:12:0, preferably 1:12:2, for flour, water, and oil. For amaranth flour the range is 1:14:8:8 to 1:0.5:0:0, preferably 1:4:1:2. For lotus flour the preferred ratio is 1:10:4:2.

In another embodiment, a product such as cookies can be prepared from white sweet potato flour, water, oil, small amounts of salt (optional), sweeteners (optional), and small amounts of any conventional leavening agents in proportions ranging from 4:1:0 to 0.5:1:2, by weight, preferably 1.8:1:0.9 in processes of mixing, kneading, shaping, baking to produce cookies. Baking conditions range from 275–500° F. preferably 350° F., and 2–40 minutes preferably 8–10 minutes. Processes are as described above for uncooked yam flour, for other flours exceptions are as noted. For cassava flour the range is 4:1:2 to 0.5:1:0, preferably 1.6:1:0.3. For malanga flour the preferred ratio is 2.4:1:0.7. For cooked yam flour the range is 4:1:0 to 0.3:1:1, preferably 0.75:1:0.3, where flour is frozen and water is boiling, and where preferred baking temperature is 400° F. For amaranth flour the preferred ratio is 2.5:1:0.4. For lotus flour the range is 6:1:0 to 0.5:1:6, preferably 3:1:2.4.

Alternatively,. when a liquid sweetener is used, the proportions are within the ranges described above, preferably 1:1.5:0.3 and 0.24 parts honey or other liquid sweetener per 1 part flour. Sweetener amounts may range from 0–1 part per 1 part flour. Alternatively, add toppings as desired to the unbaked or baked dough. Any desired fruit, nuts, flavors,. seasonings, sweeteners of the conventional art may be incorporated. Processes are as described above for yam flour, with exceptions as noted. For malanga flour the preferred ratio is 3:1:0.6 and 0.3 parts honey or liquid sweetener per one part flour. Similarly, honey or liquid sweeteners may be used with the other flours in processes of preparing cookie doughs.

In yet another embodiment, crackers may be produced in any suitable machine for mixing heavy doughs through processes involving combining flour, water, and oil in proportions ranging from 3:1:4 to ¼:1:0, preferably 1:1:1/6 parts flour, water, and oil and small amounts of salt and leavening agents. In processes including but not limited to molding, rolling, cutting, and extruding, shape dough into desired cracker shapes. Dough may or may not be coated with a thin film of oil and salt. Any conventional heating method may be used, for example bake at 350° F. for 20 minutes. Processes are as described above for other flours, with exceptions as noted. For cassava flour the range is 4:1:4 to ¼:1:0, preferably 1.7:1:1/8. For malanga flour the preferred ratio is 1.3:1:1/5. For yam flour the preferred ratio is 1:0.7-1:1/6 parts flour, boiling water, and oil. For amaranth flour the range is 6:1:4 to ¼:1:0. preferably 2.5:1:¼. For lotus flour the range is 4:1:4 to ¼:1:0, preferably 1.7:1:1.8.

In another embodiment of the invention a product such as tortillas or chips can be prepared by blending white sweet potato flour with water, and then baking or frying the appropriately shaped dough. In preparing the mixture a range from ¼:1 to 2:1 amounts of flour and water are blended, preferably 0.9:1 flour and water. The dough may be cooked by any desired means including but not limited to frying with or without oil, and baking with or without a thin film of oil, following the conventions of the art. Processes are as described above for other flours, with exceptions as noted. For cassava flour the range is 0.5:1 to 4:1, preferably 1.7:1. For malanga flour the preferred ratio is 1:1. For yam flour the range is 0.5:1 to 4:1, preferably 2:1. For amaranth flour the range is 0.5:1 to 4:1, preferably 1.6:1. For lotus flour the preferred ratio is 1.2:1.

In still another embodiment of the invention, a food product such as pie crust is prepared by blending flour, water, and oil in ratios of 1:0.41.5:0.1-1, preferably 1:0.7:0.3. Once the blend is prepared, it is kneaded shaped or molded and baked if desired at temperatures ranging from 275 to 500° F., preferably 350° F. for from 2 to 45 minutes, preferably 10 minutes. Processes are as described above for other flours, with exceptions as noted. For cassava flour the range is 1:0.4-5:0.1-1, preferably 1:2.5:0.35. For malanga the preferred ratio is 1:0.9:0.3. For yam the range is 1:0.2-1.5:0.1-1, preferably 1:0.5:0.3. For amaranth the preferred ratio is 1:0.7:0.4. For lotus the preferred ratio is 1:0.5:0.3.

In yet another embodiment, doughs from processes described earlier for pie crust and pasta may be used to produce a puffed product by shaping the dough into flat, thin wafers and frying the wafers in hot oil to produce a puffed or popped product. The dough may be shaped into a wafer or any other shape desired by combinations of extruding or other shaping means, rolling, cutting and other techniques in any order in any desired combination and fried. By this method shapes of a 'chip' or 'fry' may be obtained. Also long pieces may be shaped into a pretzel-like shapes and fried. Processes are as described above for other flours, with the exception of yam flour which becomes strongly flavored or bitter when used by this process.

A puffed product may also be obtained when white sweet potato flour is combined with pureed, cooked white sweet potato. Although almost any desired combination may be used ranging from 5-100% flour, 0-95% cooked, and pureed white sweet potato, 0-50% water, the ratios for pie crust combined with an added 20% cooked pureed white sweet potato is preferred. Either of the above processes may be used to produce very small-sized ⅛"-1" wafers, flakes and granules which can be used as a cereal product. Processes are as described above for other flours, with the exception of yam flour which becomes strongly flavored or bitter when used by this process.

In yet another embodiment of the invention, pretzels may be prepared from the doughs described for tortillas, chips, and pie crusts in processes of shaping, optional salting, and various combinations of baking with or without a thin coat of oil, frying, broiling, steaming, drying common in the food art to produce a pretzels of desired sizes and shapes. Additional embodiments include the pretzels above to which have been added to dough before baking or to the outside surface before or after baking, a variety of fillers, extenders, binders, flavorings, seasonings, preservatives and the like common to the art. Processes are as described above for the other flours.

In yet another embodiment, the thick dough produced by the processes described in the preparation of pie crust may be used to produce dough encased or wrapped food products. The kneaded, thoroughly mixed dough may be shaped by extruding, rolling, cutting, and any other convenient technique to produce a variety of shapes onto which pureed fruit, chopped meats, hot dogs, meat and vegetable combinations, cheese and the like may be placed. For example the thick dough may be shaped into 3×3×¼ inch squares onto which a pureed fruit such as sapote or carambola, and any other unusual or common fruit, are placed. These may be baked, broiled, or fried as is or 2 squares may be placed together such that the fruit forms a middle or inside layer in a sandwich-type effect. This may be baked, broiled, or fried to produce a product or may be frozen for sale to the consumer as a frozen product. Processes are as described above for the other flours.

In another example, conventional art may be used to completely encase fruit or meat and vegetable mixtures. The dough covered product which may have any shape, commonly an ovoid shape ranging from 1 inch to 6 inches in length may be baked, boiled, broiled, fried and so forth in any conventional means to produce good tasting, convenient foods. Processes are as described above for the other flours.

The dough may also be used in pot pie-type products. Processes are as described above for the other flours.

In another example, pureed or flaked meat may be combined with a small amount of imitation mayonnaise in approximate proportions of 2:1 and placed on a 6×6×¼ inch dough square. The dough is rolled around the meat mixture to form a tamale-like shape. This product may be baked, broiled, fried, or frozen. If uncooked meats are used, the product should be cooked by means other than frying. Processes are as described above for the other flours.

In another embodiment, white sweet potato flour may be combined with a vegetable oil such as sunflower oil, olive oil, or the like in amounts ranging from ¼:1 to 4:1, preferably 1.8:1 to which is added a gelatinized flour-water mixture which contains flour and water in proportion ranging from 1:1 to 1:30, preferably 1:6 to produce a white sweet potato imitation nut butter-type product. The flour and oil mixture and flour and water mixture are combined in amounts by volume ranging from 20:4 to 20:0, preferably 20:1. Processes are as described above for lotus, for other flours exceptions are as noted. For cassava flour the preferred ratio is 2.3:1. For malanga flour the preferred ratio is 1:5.4 for the gelatinized material. For amaranth flour the preferred ratio is about 2:1. For yam flour the range is 1:1 to 4:1. preferably 2.3:1.

The flour may be combined with various ingredients to prepare a colloidal product having the consistency of mayonnaise. The mayonnaise-like product itself is rather bland in taste, and it takes on the flavoring characteristics of the material blended with it in its end use—e.g. tuna fish, potato salads, sandwich meats. Flour, water, and oil are combined in ratios of 0.5-3:- 1-15:1-15, preferably in ratios of 1:9.5:5. The flour and ¼ to all of the water, preferably all of the water are combined and heated by any convention of the art to such temperature and for sufficient time to completely gelatinize the starch granules. This mixture in steps of cooling (optional) and high speed blending with any remaining water, oil, and starchy tuber to produce a colloidal product to which may be added any acid, such as lemon juice, citric acid, ascorbic acid, acetic acid and the like in amounts ranging from 0-2 parts acid to 1 part original flour used, about 0.6:1 is preferred. The mayonnaise has the colloidal properties of mayonnaise, with no other added ingredients. The mayonnaise produced by the above process has the advantage of being able to be frozen and thawed without destroying or significantly altering the colloidal properties of the product. Processes are as described above for other flours, with exceptions as noted. For cassava flour the range is 0.1-3:5-15:1-10, preferably 1:10.5:4.6. For malanga flour the preferred ratio is 1:8.6:3.8. For yam flour the range is 1:4-12:0.5-10, preferably 1:8.5:3.8. For amaranth flour the range is 0.5-3:0.2-6:0.2-10, preferably 1:1.2:1.4. For lotus flour the range is 0.5-3:2-15:0.5-10, preferably 1:8:2.7.

In another embodiment of the invention custard-type products may be produced. When flour and water are combined in proportions ranging from 1:1 to 1:30, preferably 1:6, and heated with stirring until gelatinized to a thick paste-like glue and subjected to blending in a high speed blending device with the addition of oils in proportions ranging from 0:1 to 3:1, preferably ½ part oil per 1 part original flour by weight, this process produces white, creamy fluids of various thicknesses with properties similar to evaporated milk, which when allowed to stand with or without cooling, will solidify to produce products with properties very similar to custards. These custard-type products may be used without modification as custards. In another embodiment the fluids may be combined with vegetables such as peas, corn, and squash to form custards commonly called corn puddings and the like. The fluid may be combined with pureed vegetables such as corn, pumpkin, and squash to produce custard-like pies, and with fruits such as peaches, apricots, coconut, and bananas to form creamed pies and the like. Processes are as described above for other flours.

One of the advantages of these products is that they do not require further cooking to produce the "setting up" and when combined with precooked vegetables, etc. do not need additional baking or other heat treatments.

In another embodiment of the invention, a product such as a pudding can be prepared by blending flour, water, oil, and pureed cooked fresh white sweet potato in proportions ranging from 1/7:10:6 to 1/7:1/2:1/10, preferably about 1/7:2:1. The product is produced in processes where as a first process step the flour and from 10 to 100%, preferably 50% of the water are combined and heated by any convention of the art to produce a thick gelatinized paste. This paste is then combined with the remaining raw materials and blended to a smooth, homogenous, mixture by conventional mixing techniques. Without additional ingredients the product has a sweet, pleasant taste. Processes are as described above for other cassava and malanga flours with exceptions for other flours as noted. For yam the range is 0.01:1:1/6 to 1:1:5, preferably about 1/27:1:0.8 for flour, water, and pureed cooked yam; as a first process step the yam flour and from 3-100%, preferably 10-50% of the water are combined and heated before blending with remaining ingredients. For amaranth flour the range is 1:10:6 to 1:0.5:0.1. preferably about 1:3:0.36. For lotus flour the range is 0.02:1 to 2:1, preferably about 1/10:1 for flour and water.

Alternatively, a pudding-type product may be prepared using flour and water only, in proportions ranging from 1:1 to 1:30, preferably 1:6. The ingredients are combined, heated by any conventional techniques until the mixture is completely gelatinized. Cool to between 30-0° C., preferably 10-20° C. until the consistency of pudding. Processes are as described above for other flours, with exceptions as noted. For malanga flour the preferred ratio is 1:5.4. For yam flour the preferred ratio is 1:10.6.

In still another embodiment, in processes as are described for pancakes; flour, water, oil, baking powder, and salt are combined in proportions preferably of 6:11:1, but ranging from 8:12:1 to 4:5:1 for flour, water and oil to produce a crepe-type product. The batter may be used by techniques known to the art when cooking and using batter for crepes. Processes are as described above for cassava and lotus flours, with exceptions for other flours as noted. For malanga flour the range is 1:4:0 to 1:1:0.5, preferably 1:2:1/7. For yam flour the range is 8:12:1 to 4:5:1, preferably 6:11:1.

In yet another embodiment, a sweet potato pie may be made entirely from sweet potatoes, water, flour, oil, and optional spices and sweeteners in proportions of about 6:6:1:¼. in processes where part of the flour and water are cooked separately to produce an egg replacement agent and additional combinations of water, flour and oil are cooked and blended separately to form the light cream substitute, these two substitutes are then combined with the remaining ingredients to produce a sweet potato custard-type pie filling which is poured into a white sweet potato pie crust. Temperature ranges from 250 to 425° F., with times of cooking ranging from 30 to 75 minutes. Preferably the pie is baked at 400° F. for 20 minutes or until crust is browned and filling is bubbling. Filling may also be placed in precooked pie crust and served with no baking after filling has cooled and set up. Baking of the filling is actually unnecessary.

In still another embodiment of the invention, when a given amount of white sweet potato flour is mixed with water of a temperature range from 0 to 150° C., 100° C. is preferred, in proportions ranging from ¼ to 4 parts flour per part water, preferably 1⅓ parts flour per part water, a dough can be prepared, which, after maintaining a heating and kneading period of from 0 to 10 minutes, preferably 1 minute, followed by extruding, cutting and drying, prepares such products as noodles, pastas and the like. It is also possible to mix the batter prepared with baked camote or other farinaceous and mealy textured tubers and possibly other vegetable matter in the amounts to produce stiff doughs for gnocci, hard dumplings, and other pasta products. In another embodiment of the invention, a thick gelatinized paste of cooked white sweet potato flour and water comprised of preferably 1:6 parts flour and water, with acceptable ranges of 1:2–30, may be added to the above described dough mixture before extrusion to any desired pasta shapes, to produce substitutes for egg based pasta. Processes are as described above for cassava and lotus flours, with exceptions for other flours as noted. For malanga flour the preferred kneading time is 2 minutes. For yam flour the preferred ratio is 1 part flour to 1 part water. For amaranth flour the preferred water temperature is about 25° C.

In a further embodiment of the invention, the pasta doughs described above, with or without the egg-substitute may be heated at temperatures above 50° C. for 2–30 minutes, preferably 2–5 minutes at 95° C. to gelatinize a part of all of the dough prior to extrusion. Processes are as described above for other flours.

The pastas thus described are dried by any conventional means, preferably air dried on trays to produce a final product.

In its final uses, this pasta does not swell significantly beyond its dried size, when cooked in boiling water and the like. This is due to the fiber content which has been retained in the flour. These fibers prevent the typical swelling and conversion to a jelly-like mass common to noodles from most pure starches. Thus these pasta products retain a form and consistency similar to wheat based noodle products. They may be used in all ways any other noodles are used.

In another food embodiment, the white sweet potato flour can be combined with water in a ratio of 12:1 to 3:1 parts by volume water per unit volume of flour, preferably 6:1 water to flour, and a small amount of a vegetable oil to produce a white sweet potato milk. Preferably half of the flour and water are combined (actual amounts may range from 10–80% flour and 25–100% water), heated by conventional methods until the mixture is completely gelatinized. The gelatinized mixture and remaining ingredients are combined, thoroughly mixed in a high speed blending device to produce a white sweet potato milk or other similar fluid mixtures. Processes are as described above for cassava and lotus flour, for other flours exceptions are as noted. For malanga flour the preferred ratio is 5:1 water to flour, preferably ¼ of the flour and water are combined and heated. For yam flour the preferred ratio is 5.3:1. For amaranth flour the preferred ratio is 6.5:1. For cooked malanga flour the range is 1:2 to 1:8, preferably 1:4 combined with a small amount of salt.

In the above embodiment, flour of almost any particle size may be used ranging from very coarse to very fine. The particle size is not important for that portion of the flour used for gelatinization, although fine flours are preferrable. A more finely divided flour product is desired for the flour that remains uncooked in the milk. The smaller the particle sizes, the better, preferably at least less than 0.001 inch. The milk produced from very fine flours does not require straining to yield a smooth homogeneous product. Larger particle sizes produce a gritty product that must be strained before use. The larger the particle sizes, the greater proportion of white sweet potato flour that is removed by straining, and the more separation into layers that occurs on setting. Processes are as described above for other flours.

In another food embodiment, white sweet potato flour can be combined with water in proportions ranging from 1:1 to 30:1 parts by volume of water per unit of flour, preferably 3:1 water to flour for heavier creams and 6:1 for lighter creams, and a small amount of a vegetable oil. 50 to 100 per cent of the flour is combined, and heated until the mixture is completely gelatinized. The gelatinized mixture and remaining ingredients are combined, thoroughly mixed in a high speed blending device to produce substitutes for light to heavy creams and condensed milk. Processes are as described above for other flours cassava, malanga, amaranth, and lotus, with exceptions as noted. For yam flour the preferred ratio for heavier creams is 5:1 and for lighter creams is 10:1.

In another embodiment of the invention, white sweet potato flour may be combined with water in amounts from 1:½ to 1:6, preferably 1:1½, a small amount of oil, and crushed ice to prepare milk shake and ice cream-like products. From ¼ to ¾ of the flour, preferably ½ the flour used is combined with water heated by any convenient means until thoroughly gelatinized, then combined with remaining flour, crushed ice, and a small amount of oil in a suitable blending device to produce a thick milk shake-like slurry product. The white sweet potato milk shake has a pleasant taste without further additions, but may also be flavored with any fruits, nuts, sweeteners, or other flavors to produce many flavors and blends. Processes are as described above for cassava, yam, and lotus flours.

In another embodiment the above milk shake-like product may be used in processes of freezing, comminuting, in one or two freezing and comminuting cycles, to produce a product blended to a creamy consistency of ice cream. The white sweet potato ice cream has a pleasant taste without further additions, but may also be flavored with any fruits, nuts, sweeteners, or other flavors to produce many flavors and blends. This product may also be used as an ingredient in more conventional ice cream preparations. In another embodiment, a more creamy ice cream and milk shake product may be produced by increasing the amount of fat or oil in the product. Processes are as described above for flours of white sweet potato, cassava, malanga, yam, amaranth, and lotus.

In other embodiments of the invention, the finely divided flours of white sweet potato, cassava, malanga, yam, amaranth and lotus may be employed as a thickener, filler, or extender in the preparation of hypoallergenic cosmetics, and industrial products. For example, white sweet potato flour of fine particle sizes may be used in dusting powders and face powders. Various shades may be obtained by heating and toasting methods. This produces a face powder product which could be well tolerated because people would be only placing nonallergic items on their faces. Similar powders may also be used as bases for liquid and paste makeups to produce hypoallergenic products. The cosmetic preparations may also be prepared with any desired combinations of white sweet potato flour with conventional ingredients including but not limited to other flours, extenders, binders, fillers, preserving agents, and so forth.

In another embodiment, the dried shreds from peeled or unpeeled, preferably peeled, cooked white sweet potato, cassava, malanga, yam, and lotus may be used to produce a shredded cereal product. Alternatively, the above cereal products are made by freezing the cooked tubers before shredding and drying. This produces a softer shred with improved properties which is better for eating and comminuting for flour.

The flour from dried, cooked camote of various particle sizes may be coarsely ground to produce a creamed cereal product and finely ground to produce instant mashed white sweet potato products. In final use, each product is combined with water in ratios of 1:2-10, preferably 1:5, and heated for 2 to 10 minutes at temperatures from 75 to 100° C., preferably 100° C. in processes of rehydration and cooking. Processes are as described above for cassava, malanga, and lotus flours, with exceptions for other flours as noted. For yam flour the range is 1:5-15. preferably 1:10 for creamed cereal and 1:7 for instant mashed yam.

The cooked white sweet potato flour may also be used in combination with the raw white sweet potato flour in many of the products and processes described previously, and may also be used with many other types of flours. Processes are as described above for the other flours.

Yet another embodiment involves processes to produce a hypoallergenic infant formula. Many infants are unable to tolerate the currently available infant formulas. Infants unable to tolerate the grains, legumes, milk products, eggs, and grain-derived sugars listed earlier along with coconut oil are almost certainly going to be intolerant of all commercially available infant formulas. These infants are usually unable to tolerate breast milk because of allergies to digested food residues in the milk. The parents of these infants desperately seek alternatives and usually end up using cooked purees of tubers and other foods. There is a real need for infant formulas without grains, legumes, grain-based sugars, milk and milk products, and coconut or corn oil. No truely hypoallergenic formula exists at present. Processes are as described above for the other flours.

The earlier described process for producing white sweet potato milk, in which finely powdered, precooked, dried white sweet potato flour is substituted for the raw flour may be used to produce infant formulas. In one infant formula embodiment the just described formula is used without further modification in either full fluid form, condensed form, or dry powdered form a hyperallergenic formula to which the user would add pureed, cooked protein in the amount of about 2.5 g protein per quart of fluid, and 40 g of fat per quart of fluid fully reconstituted. This would be ideal for many infants since the protein and fat sources could be varied by the parents according to the physician's instructions and specific allergies of the infant. This would assure the broadest tolerance of the formula. Processes are as described above for the other flours.

The tubers such as white sweet potatoes are highly nutritious in vitamins and minerals, and the white variety does not have the problems of excessively high vitamin A levels as does the orange sweet potato variety and is therefore an excellent choice for hypoallergenic formulas. Malanga are highly nutritious in vitamins and minerals, and because they are almost universally well tolerated, malanga is an excellent choice as a base for hypoallergenic formulas. Yams are highly nutritious in vitamins and minerals and are therefore an excellent choice for hypoallergenic formulas.

In another embodiment of the invention, a more complete infant formula may be obtained by adding the appropriate amounts of protein and carbohydrates to the above described formulas. Any protein and fat source is included in the embodiment as part of the product and process, preferably for hypoallergenic purposes beef, milk, pork, eggs, lamb, goat, and legume sources would not be used; obscure protein sources such as venison, rabbit, even fish are much more suitable, as fat source sunflower oil is preferred although any oil or other desired fat source can be used. The art is aware of previous infant formulas available as ready-to-feed, liquid concentrate and dry powder; the above described hypoallergenic formulas may be prepared in such forms. Processes are as described above for the other flours.

Many variations in the above formula are possible by varying amounts of oil, water, white sweet potato, cooked versus uncooked flours, added ingredients and so forth, all are hereby included in the embodiment. The infant formula may also be prepared with white sweet potato flour and combinations of conventional ingredients including but not limited to other flours, extenders, binders, fillers, preserving agents, sweeteners, flavorings, seasonings, eggs, milk, nuts, and so forth. These are hereby included in the embodiments. Processes are as described above for the other flours.

In another embodiment, white sweet potato flour may be used in a wide variety of pharmaceutical products as a hypoallergenic filler, extender, and inert ingredient. The use of a hypoallergenic material for these purposes would eliminate allergic reactions that food allergic patients may have to the nonactive ingredients, would thereby enhance the number of persons who tolerate the pharmaceutical products and could help the medications to be more effective for the allergic patient. Processes are as described above for the other flours.

Finally, to promote complete utilization of the entire white sweet potato tuber, the white sweet potato may be used in processes to produce animal feed products. An animal feed is prepared by drying the peels of white sweet potatoes (entire tuber if desired) by any of various methods, and then the peels are comminuted to a particle size ranging from $\frac{1}{8}$-174 inch to a powder by any conventional means desired. The comminuted material is then combined with from 2 to 40% of any suitable fatty material, 0-8% of any suitable protein source, and with vitamins and minerals added as desired. The substance obtained may be used directly as an animal feed, in ratios ranging from 5:1 to 1:100 with other animal feed products, preferably 1:5. Alternatively, the above white sweet potato product may be combined with the remainder of the sweet potato plant, i.e., dried comminuted leaves and vines to produce a feed. Processes for lotus are also as described above. For cassava, malanga and yam processes are as described above with the further incorporation of processes conventional to the art for reducing levels of toxic alkaloids and the like in the tubers.

Although I have developed a series of products to provide the most hypoallergenic products, it is within the scope of this invention to include conventional additives and additional ingredients used in other such products, including but not limited to grain flours and other flours, other flour products starches, and flours of the instantly claimed invention, eggs, milk and milk products, nuts, other fat sources, legumes, fruits, vegetables, extenders, binders, chemical modifiers, fillers, preserving agents, sweeteners including sugar and other conventional sweeteners, flavorings, seasonings, yeast as a leavening agent, and so forth.

The preferred embodiments presented above are for a flour of about 5% or less, more preferably about 3% moisture, of generally fine particle size (except in applications where obviously a coarse particle size is desired), and for hypoallergenic products where limited ingredients are desired. The preferred embodiments above change according to the water content of the flour; as the amount of water in the flour increases, the amount of water to be added to the flours decreases. Also optimal proportions change with the degree of fineness of the flour, with amounts of various additives, especially chemical modifiers and the like, and with various flour mixtures. All such embodiments are hereby incorporated with this embodiment.

Similarly, the preferred embodiments described above have been developed in such a way that any desired oil may by used in the processes described. Very little in the way of adjustment is select from among the many oils available. The selection of a given oil will have very little effect on the texture or structure of a baked product. Oils which are strongly flavored may provide the predominant flavor of a finished product, however. Other fat sources such as shortenings and animal fats are also hereby incorporated with this invention.

While the flours of the present invention are described individually, it is clear that they may generally be mixed with each other as well as any other more conventional flours such as wheat, corn, millet, milo, soy, lentil, and the like, and any other non-conventional flours such as arrowroot, water chestnut, artichoke flours, and the like, in processes suitably modified according to the individual characteristics of each flour.

Although I have described the foregoing embodiments in the nature of providing wholly or partially hypoallergenic flours and food products, it is to be understood that the present invention includes the discovery o heretofore unrecognized food sources. The foregoing flours may thus be added as a partial substitute for previous known flours.

The above described white sweet potato flours have further been found to exhibit flavor enhancing properties. While not providing much in the way of noticeable flavors of their own, they enhance the flavors of other ingredients. This is particularly noticeable when such flours are included in products containing meats, nuts, fruits, vegetables, and sauces. Therefore white sweet potato flours are particularly desirable as additives to meats, cookies, muffins, pies and the like. All such flavor enhancing properties are hereby incorporated with this embodiment.

The taste, flavor, texture, consistency, structure and the like of each flour changes significantly and sometimes suprisingly when used in the various processes described in the instantly claimed invention. In some cases the flavors are virtually identical to that of the fresh tuber or seed from which the flour is prepared. In many cases, however, unique and suprising tastes result. It is not possible to predict prior to preparation what the taste will be. For example when white sweet potato flour is used in various processes, the pastas taste much like the parent tubers, the breads have a light pleasant taste not like that of the parent tubers, and the cookies, nut butter, and toasted shreds taste very much like peanuts. When malanga flour is used in various processes, the pastas taste virtually identical to wheat pastas, the pancakes taste much like potato pancakes, and the cookies and bread have a moderate to moderately strong taste that can be almost bitter. The lotus flours and flour products have a flavor of sharp cheddar cheese with a very slight hint of lemon; although suprising if not expected, the flavor is pleasant. This flavor changes very little among the products of lotus, and it is therefore suitable as a flavoring ingredient. The unique, suprising, and individual tastes of each product described are hereby incorporated in this embodiment.

Similarly, as for taste and flavor, the texture, consistency, structure and the like of each flour changes significantly and sometimes suprisingly when used in products of the instantly claimed invention. It was not possible prior to preparation, to predict what such properties as texture, consistency, structure and the like would be. Some products change dramatically in structure and texture according to temperature changes. For example the texture of white sweet potato bread increases in firmness at cold temperatures, but becomes soft, flexible, and very similar to wheat breads in texture when warmed slightly; and yet the texture of pancakes made from white sweet potato flour is similar to that for wheat pancakes and does not change significantly with temperature. Some products when eaten are very filling and satisfying even when small portions are eaten, making them very well suited for uses as dieting aids; white sweet potato muffins are a good example of this. Other products of the same flour do not seem to have this property, and are ideal for those who need to gain weight; white sweet potato nut butter substitutes are a good example. The unique, suprising, and individual texture, consistency, structure, and the like of each product described herein is hereby incorporated in this embodiment.

Many of the products of the instantly claimed invention are satisfying and filling, and provide sustained energy for several hours without causing hunger, or energy peaks and sags. The uses for snack foods, foods for athletes, and the like are hereby included in this embodiment.

Many of the products described above are well suited for the preparation of packaged dry mixes, frozen products and the like, all such products and processes are incorporated with this embodiment.

It is of course within the scope of this invention to add additional fiber to that naturally present in the tubers, to the white sweet potato, cassava, malanga, yam, amaranth, quinoa, lotus, arrowhead, buckbean and other flours of the present invention to provide further improved properties of the flours and products produced from the flours. Such additional fiber may be from the same tuber or seed, or may be from a different tuber or seed, and said fiber may be from other fiber sources conventional to the art. Such embodiments are hereby included in the invention.

It is further possible to assemble flours with properties of the described invention by combining pulverized starches obtained from the above tubers and seeds and pulverized fibrous materials from various sources. Such flour embodiments are hereby included in the preferred embodiments.

As is evident from the above discussion, the central objective of the present invention is to provide a variety of different foodstuffs, the basis for all of which is a tuberous plant, which is well tolerated by many persons with multiple allergies, hence the term hypoallergenic. Thus, insofar as the flour obtained from the tuber is mixed with other ingredients which do not detrimentally affect the hypoallergenic properties of the food product obtained, hypoallergenic foodstuffs of different sorts can be obtained by the techniques described above. On the other hand, it is recognized that other ingredients can be added to the flour used in the present invention which produce useful foodstuffs of still different qualities. The present invention also embraces these hyperallergenic foodstuffs, and therefore the present invention is not limited to just hypoallergenic foodstuffs.

Having generally described this invention, a further understanding can be obtained by reference to certain specific examples which are provided herein for purposes of illustration only and are not intended to be limiting unless otherwise specified.

EXAMPLE NUMBER 1: WHITE SWEET POTATO BREAD

Place 453 g white sweet potato flour in a suitable conventional mixing device. Slowly add 623 g water and 3.25 g salt while mixing at lowest speed. When well blended mix at highest speed for about 1 minute. Stir in 47 g baking powder; then mix at high speed for 15 seconds. As fast as possible pour into baking pan. Carefully place in oven heated to 425° F. and bake for 50 minutes. The amount of water needed varies with the moisture content and particle size of the flour. More coarse flour and/or flour with a lower moisture content will require more water. The resultant white sweet potato bread product may be used in any way wheat bread is used.

EXAMPLE NUMBER 2: WHITE SWEET POTATO IMITATION CORNBREAD

Ingredients: 304.8 g white sweet potato flour, 453 g water, 23.6 g white sweet potato baking powder, 6.5 g salt, 12.5 g oil. Combine above ingredients with baking powder added last; mix well, at highest speed with conventional mixing equipment until well blended and uniform consistency, about 1 minute. Transfer quickly into suitable baking container and bake 20–25 minutes at 425° F. Alternatively, the following proportions may be used in an imitation cornbread with honey or other liquid sweetener: 343 g white sweet potato flour, 396.4 g water, 6.5 g salt, 75 g honey, 23.6 g white sweet potato baking powder, 12.5 g oil.

EXAMPLE NUMBER 3: WHITE SWEET POTATO CAKE DOUGH 343 g white sweet potato flour, 396.4 g water, 90 g honey, 35 g oil, 35.4 g suitable leavening agent, may be combined in the processes described in Example 2. Dough may be baked as described in Example 2, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 4: WHITE SWEET POTATO MUFFINS

Combine 343 g white sweet potato flour, 453 g water, 6.5 g salt, 12.5 g oil, 23.6 g white sweet potato baking powder and mix well, at high speed with conventional techniques of the art until smooth and well blended. Add baking powder and mix well. Pour quickly or transfer by other means into suitable baking equipment. Bake for 20–25 minutes at 425° F.

EXAMPLE NUMBER 5: WHITE SWEET POTATO PANCAKES

The following ingredients: 304.8 g white sweet potato flour, 453 g water, 6.5 g salt, 50 g oil, 23.6 g white sweet potato baking powder, are combined and mixed well on highest speed, preferably 1–2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color. When honey or other liquid sweetener is used, the ingredients: 304.8 g white sweet potato flour, 453 g water, 6.5 g salt, 75 g honey, 50 g oil, 23.6 g white sweet potato baking powder, may be used in the process described above.

EXAMPLE NUMBER 6: WHITE SWEET POTATO PANCAKE MIX

To provide an example of a dry mix-type product, white sweet potato pancake mix is used. A white sweet potato pancake mix product can be made by combining ingredients: 453 g flour, 8.7 g salt, and 10.7 g white sweet potato baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of white sweet potato pancake mixes.

EXAMPLE NUMBER 7: WHITE SWEET POTATO PIZZA DOUGH

The batters described in Example 5 may also be used as a pizza dough.

Prepare batter as described above, pour dough onto pizza pan. Place in oven and bake at 425 degrees until dough is almost done but still tacky on the top, about 20 minutes. Add any desired ingredients, various meats, vegetables, spices, and other materials common to the art. Bake until dough is completely done and ingredients thoroughly cooked, about 10 minutes. Alternatively, the topping can be placed on the batter before cooking begins, or after cooking ends.

Alternatively, the dough described for pie crust, Example 15, may be used as a pizza dough. The dough is prepared as described in the example, the dough is rolled out to the desired length, width, and thickness, toppings of any kind are added and the mixture is baked at 350° F. for 10–30 min.

EXAMPLE NUMBER 8: WHITE SWEET POTATO WAFFLES

The following ingredients are combined by the method described above in Example 5: 304.8 g white sweet potato flour, 509.6 g water, 6.5 g salt, 50 g oil. 23.6 g white sweet potato baking powder. Pour batter into waffle iron or other suitable molding or shaping device preheated to 300–500° F. Watch for steam coming from the waffle iron as the waffles cook. Leave waffle iron closed as long as steam can be seen rising from the waffle iron. When steam stops, all water has been baked out of the batter and waffles are done, 5–10 minutes or more. When done the waffles should be golden brown in color.

EXAMPLE NUMBER 9: WHITE SWEET POTATO FRENCH TOAST

Combine 19.5 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified or combine 19.5 g flour and 226.5 g water. Heat by any desired convention until mixture is well gelatinized and thickened. Let cool. Coat pieces of white sweet potato bread. Fry to slightly browned and crusty in lightly greased griddle or skillet preheated to medium high. Alternatively french toast batter may be prepared by the method as described above without cooking the flour/water mixture. French toast batter may be used for many combinations with white sweet potato bread crumbs and many other coating materials or alone.

EXAMPLE NUMBER 10: WHITE SWEET POTATO COOKIES

Combine and mix well by the conventional art: 304.8 g white sweet potato flour, 170 g water, 6.5 g salt, 150 g oil, 12 g white sweet potato baking powder. Form into cookie shapes by the conventional art. Bake at 350°F. on ungreased surface for 8–10 minutes or until a light golden brown on the underside. Alternatively, add ingredients as desired to the unbaked or baked dough. Any desired fruits, nuts, flavors, and seasonings of the conventional art may also be used. When a liquid sweetener or honey is used, the following ingredients are combined as described above: 304.8 g white sweet potato flour, 453 g water, 6.5 g salt, 75 g honey, 100 g oil, 12 g white sweet potato baking powder.

EXAMPLE NUMBER 11: WHITE SWEET POTATO DOUGHNUTS, PRETZELS, HUSH PUPPIES, DOUGHNUT HOLES

From batter prepared in the method of Example 5, extrude batter through a doughnut press or any other desired device in rings onto hot oil; batter may also be dropped in balls, long pieces, even pretzel shapes. Temperature of the oil should be about 300–500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, and the like. Alternatively, doughnuts may include preparations of conventional ingredients including but not limited to: other flours, extenders, binders, fillers, preserving agents, flavorings, seasonings, eggs, milk, and so forth.

EXAMPLE NUMBER 12: WHITE POTATO DUMPLINGS

Combine 152.4 g white sweet potato flour, 226.5 g water, 4.9 g salt, 12 g white sweet potato baking powder until smooth and creamy. Let dough set for about 15 minutes. Drop teaspoon-sized portions of batter into about 2 liters of rapidly boiling water or broth, may be thickened. Allow to remain in boiling water 2–6 minutes, preferably 5 minutes. If dumplings remain in boiling broth longer, dumplings will dissolve. When done, dumplings will be light and tender on the inside.

NUMBER 13: WHITE SWEET POTATO BATTER

A batter prepared by the method of Example 5 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 14: WHITE SWEET POTATO CREPES

In yet another embodiment of the batter prepared in Example 5, the batter may be used to make a crepe-like product. The batter may be diluted by the addition of 10–400 g water, preferably 100 g to make a crepe-like product. The batter is spread in very thin layers on a cooking surface, and prepared according to the accepted convention.

EXAMPLE NUMBER 15: WHITE SWEET POTATO PIE CRUST

Mix thoroughly, 152.4 g white sweet potato flour, 50 g oil, 113.25 g boiling water. Shape into round, flat dough ball. By any conventional means shape into appropriate dimensions for pie crust. Preferably, place between cellophane or wax paper sheets before rolling out dough. This dough is also very well suited to shaping in a mold; it can be reshaped many times without becoming hard and leathery. White sweet potato pie crust may be used as a double or single crust pie, with any type of filling, including meat (e.g., chicken pot pie) or fruit filling. For a baked pie crust, bake for 10 minutes at 350° F.

Although above ingredients are preferred, white sweet potato flour may be used with shortening or lard and any other conventional ingredients. For example, when using lard, use about 100 g and decrease water to 10–14 g. Dough will seem stiff and hard, but will be just right after baking.

EXAMPLE NUMBER 16: WHITE SWEET POTATO TORTILLAS, CHIPS

Mix 152.4 g white sweet potato flour with 170 g water., knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 17: WHITE SWEET POTATO PRETZELS

Doughs produced by the processes described in Examples 15 and 16 may be used in processes of shaping to form pretzels of various sizes, coating with oil (optional), cooking by various processes of the art including but not limited to baking, frying, and drying to produce pretzels of varying sizes.

EXAMPLE 18: WHITE SWEET POTATO IMITATION NUT BUTTER 453 grams of white sweet potato flour are placed into any blending equipment suitable for mixing very thick doughs at very high speeds, to which is added 200-250 g edible fatty material, such as vegetable oils (preferred for hypoallergenic products) but could also include other fatty materials; add to this a paste made of 4.7 g flour and 28.4 g water that has been cooked. The materials are thoroughly mixed for about 2 minutes or until the entire mixture is well blended, and the consistency of peanut butter. Alternatively, the nut butter substitute can be made by the flour and oil mixture alone, omitting the flour and water paste.

EXAMPLE 19: WHITE SWEET POTATO IMITATION MAYONNAISE

Combine 47.6 g white sweet potato flour, 6.5 g salt, and 113.25 g cold water until well blended. Add slowly to 340 g boiling water, stirring constantly. Continue stirring until mixture is completely gelatinized and thickened; cool to about 50° F. Place mixture in conventional high speed blending device., add 200 g oil.(optional: 21.3 g lemon juice, vinegar, or ascorbic acid solution). Mix materials on highest speed until well blended, smooth, and uniform consistency. Mayonnaise will thicken as it cools.

EXAMPLE NUMBER 20: WHITE SWEET POTATO MILK

Combine 453 g water and 76.2 g white sweet potato flour; mix thoroughly. Stirring constantly, heat until well gelatinized, thick, and well blended. Blend together an additional 453 g water, 76.2 g very finely comminuted white sweet potato flour, and 37.5 g oil in any high speed blending device. Add in the cooked flour mixture. Blend 1-30 minutes at highest speeds, preferably 4 minutes. May be strained if flour not sufficiently fine.

EXAMPLE NUMBER 21: WHITE SWEET POTATO MILK SHAKE

Combine 76.2 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50° F. or lower, preferably 35° F. In high speed blending device, combine gelatinized mixture, 12.5 g oil, 76.2 g white sweet potato flour, and 226.5 g crushed ice. Blend well at speeds high enough to partially freeze mixture as ice particles become crushed and fine to form a thick slurry the consistency of a milk shake. The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 152.4 g flour, 453 g water and 12.5 g oil (226.5 g water and flour still cooked as described above) under conditions of simultaneous freezing and mixing to form a milk shake-like slurry without adding crushed ice. Similarly other methods of the art may be used to produce the frozen slurry.

EXAMPLE NUMBER 22: WHITE SWEET POTATO ICE CREAM

The milk shake-like product described in example 21 may be used as a base for ice cream products. The above slurry is subjected to freezing from 32° F. to −30° F. or lower, preferably −20-0° F., until product attains this temperature. Frozen mixture is then comminuted, and placed in high speed blending equipment and blended at highest speeds until well mixed, smooth, and creamy. Freezing, comminuting and mixing cycles may be repeated as desired, 2 such cycles are preferred. Additional embodiments described in Example 21 may also be used in this example.

EXAMPLE NUMBER 23: WHITE SWEET POTATO NOODLES

Using conventional equipment for kneading thick dough, combine 453 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays conveyors or the like. Dough may also be used to make any pasta product common in the art including but not limited to ravioli, Chinese-style meat filled noodle dumplings, and other meat-filled products.

Alternatively a small amount of flour and water, preferably 20 g white sweet potato flour and 120 g water may be cooked to a thick paste and added to the above mixture. In another alternative process, prior to extruding, the flour mixture described above which may or may not be simultaneously kneaded, may be maintained at temperatures above 50° C. for 2-30 minutes, preferably 2-5 minutes at 95° C. to gelatinize part or all of the dough.

When cooking, immerse noodles in boiling water for 2-10 minutes depending on width of noodles. Any other cooking techniques of the art may also be used. Noodles will change from off-white opaque to light brown as the starch granules gelatinize. Noodles may be used in any type pasta dish—soups, stews, pasta and sauce dishes, and the like.

EXAMPLE NUMBER 24: WHITE SWEET POTATO CRACKERS

In any suitable machine for mixing heavy doughs, combine 453 g white sweet potato flour, 453 g water 3.25 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking. frying and the like. Alternatively, omit oil, or oil and salt, increasing water by 30 grams.

EXAMPLE 25: WHITE SWEET POTATO PUDDING

Combine equal parts by volume of cooked, mashed white sweet potato and water, using 1 liter of each. The method of cooking and pureeing may be by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are blended to a thick paste by any conventional means. Separately 152.4 g white sweet potato flour is combined with 1 Kg water and heated to boiling point for 5 minutes to produce a thick gelatinized paste. The gelatinized paste is combined with the cooked tuber paste by any conventional mixing technique until well blended. The mixture is the consistency of pudding, and with the addition of no other ingredients has a pleasant, sweet taste.

Pudding can also be made by combining 453 g water and 76.2 g flour in suitable heating apparatus. As mixture reaches boiling point stir constantly. When thoroughly gelatinized, and very thick, put in high speed bleeding device and mix on high for 5 minutes. Add 25 g oil and mix again. Cool almost to freezing.

EXAMPLE NUMBER 26: WHITE SWEET POTATO PIE

1. Using the method described in Example 15, make a white sweet potato pie crust and place it in any appropriate container for baking.

2. Combine 76.2 g white sweet potato flour and 453 g water, heat the resultant mixture by any conventional means with stirring until the mixture is very thick and completely gelatinized. Place in high speed blending device and blend at highest setting for at least 5 minutes. Add 25 g oil and blend again for 1-2 minutes.

3. Combine 19.05 g white sweet potato flour and 113.25 g water, heat the resultant mixture by any conventional means with stirring until the mixture is very thick and completely gelatinized. Combine this thick mixture with the following: 500 mls cooked white or orange sweet potato puree, 188 mls any honey (optional)—dry sweeteners are also an optional ingredient, 3.25 g salt, seasonings: 4 g ground cinnamon, 2 g ginger, 1 g cloves (seasonings optional), 420 ml of the mixture obtained in step 1. Mix together by any conventional means.

4. Pour mixture into unbaked pie crust. Baking temperature and times may vary from no baking to 425° F. for 1½ hours. Preferably, bake at 350-425° F. just until filling bubbles and crust is browned. Alternatively custard will form on standing and no baking is required, thus, mixture from step 3 may also be placed in baked pie shell and cooled with no baking step. Also, repeated freezing—thawing cycles do not affect the quality of the pie filling.

EXAMPLE 27: WHITE SWEET POTATO FLOUR

Peel white sweet potatoes under running water, also removing any spots and/or undesirable areas, then free of excess water, dip briefly in distilled water, again remove excess; do not soak. Shred to desired size, place on glass or metal trays; air dry at 145° F. for 8-12 hours, preferably 10 hours. Comminute shreds with any desired technique that incorporates most of the fiber, 100% utilization is preferred, into the flour product that is a fine flour of relatively uniform particle size distribution.

EXAMPLE 28: COOKED WHITE SWEET POTATO FLOUR

The method of example 28 is used to produce a cooked flour product, with the added process of heating the white sweet potato tuber with steam until gelatinized, and then proceeding with shredding and drying steps.

EXAMPLE NUMBER 29: CASSAVA BREAD

Place 572 g cassava flour in a suitable conventional mixing device. Slowly add 509.6 g water while mixing at lowest speed. When well blended mix, at highest speed for about 1 minute. Stir in 34.14 g baking powder; then mix at high speed for 15 seconds. As fast as possible pour into baking pan. Carefully place in oven heated to 425° F. and bake for 40 minutes. The amount of water needed varies with the moisture content and particle size of the flour. More coarse flour and/or flour with a lower moisture content will require more water. The resultant cassava bread product may be used in any way wheat bread is used.

EXAMPLE NUMBER 30: CASSAVA IMITATION CORNBREAD

Ingredients: 286 g cassava flour, 339.75 g water, 16 g cassava baking powder, 6.5 g salt, 37.5 g oil. Combine above ingredients with baking powder added last; mix well, at highest speed with conventional mixing equipment until well blended and uniform consistency, about 1 minute. Transfer quickly into suitable baking container and bake 20-25 minutes at 425° F. Alternatively, the following proportions may be used in an imitation cornbread with honey or other liquid sweetener: 286 g cassava flour, 339.75 g water, 6.5 g salt, 46.9 g honey, 16 g cassava baking powder, 31.25 g oil.

EXAMPLE NUMBER 31: CASSAVA CAKE DOUGH 286 g cassava flour, 339.75 g water, 46.9 g honey, 31.25 g oil, 22 g suitable leavening agent, may be combined in the processes described in Example 30. Dough may be baked as described in Example 30, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 32: CASSAVA MUFFINS

Combine 286 g cassava flour, 340 g water, 6.5 g salt, 37.5 g oil, and mix well, at high speed with conventional techniques of the art until smooth and well blended. Add 16 g leavening agent. Pour quickly or transfer by other means into suitable baking equipment. Bake for 20-25 minutes at 425° F.

EXAMPLE NUMBER 33: CASSAVA PANCAKES

The following ingredients: 429 g cassava flour, 453 g water, 6.5 g salt, 43.75 g oil, 23.6 g cassava baking powder, are combined and mixed well on highest speed, preferably 1-2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color. When honey or other liquid sweetener is used, the ingredients: 429 g cassava flour, 453 g water, 6.5 g salt, 46.9 g honey, 31.25 g oil, 23.6 g cassava baking powder, may be used in the process described above.

EXAMPLE NUMBER 34: CASSAVA PANCAKE MIX

To provide an example of a dry mix-type product, cassava pancake mix is used. A cassava pancake mix product can be made by combining ingredients: 572 g flour, 8.7 g salt, and 10.7 g cassava baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of cassava pancake mixes.

EXAMPLE NUMBER 35: CASSAVA PIZZA DOUGH

The batters described in Example 33 may also be used as a pizza dough Prepare batter as described above, pour dough onto pizza pan. Place in oven and bake at 425 degrees until dough is almost done but still tacky on the top, about 20 minutes. Add any desired ingredients, various meats, vegetables, spices, and other materials common to the art. Bake until dough is completely done and ingredients thoroughly cooked, about 10 minutes Alternatively, the topping can be placed on the batter before cooking begins, or after cooking ends. Alternatively, the dough described for pie crust, Example 43, may be used as a pizza dough. The dough is prepared as described in the example, the dough is rolled out to the desired length, width, and thickness, toppings of any kind are added and the mixture is baked at 350° F. for 10-30 minutes.

EXAMPLE NUMBER 36: CASSAVA WAFFLES

The following ingredients are combined by the method described above in Example 33: 429 g cassava flour, 453 g water, 6.5 g salt, 43.75 g oil, 23.6 g cassava baking powder. Pour batter into waffle iron or other suitable molding or shaping device preheated to 300-500° F. Watch for steam coming from the waffle iron as the waffles cook. Leave waffle iron closed as long as steam can be seen rising from the waffle iron. When steam stops, all water has been baked out of the batter and waffles are done, 5-10 minutes or more. When done the waffles should be golden brown in color.

EXAMPLE NUMBER 37: CASSAVA FRENCH TOAST

Combine 17.9 g flour, 6.5 g salt, and 283.1 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified or cook 226.5 g water and 17.9 g cassava flour until gelatinized and thickened. Coat pieces of cassava bread. Fry to slightly browned and crusty in lightly greased griddle or skillet preheated to medium high. Alternatively french toast batter may be prepared by the method as described above without cooking the flour/water mixture. French toast batter may be used for many combinations with cassava bread crumbs and many other coating materials or alone.

EXAMPLE NUMBER 38: CASSAVA COOKIES

Combine and mix well by the conventional art: 357.5 g cassava flour, 226.5 g water, 6.5 g salt, 100 g oil, 8 g cassava baking powder. Form into cookie shapes by the conventional art. Bake at 350° F. on ungreased surface for 8-10 minutes, or until a light golden brown on the underside. Alternatively, add toppings as desired to the unbaked or baked dough. Any desired fruit, nut, flavors, seasonings of the conventional art may also be used. When a liquid sweetener or honey is used, the following ingredients are combined as described above: 357.5 g cassava flour, 226.5 g water, 6.5 g salt, 50 g honey, 50 g oil, 8 g cassava baking powder.

EXAMPLE NUMBER 39: CASSAVA DOUGHNUTS, PRETZELS, HUSH PUPPIES, DOUGHNUT HOLES

From batter prepared in the method of Example 33, extrude batter through a doughnut press or any other desired device in rings onto hot oil; batter may also be dropped in balls, long pieces, even pretzel shapes. Temperature of the oil should be about 300-500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, etc. Alternatively, doughnuts may be preparations of conventional ingredients including but not limited to: other flours, extenders, binders, fillers, preserving agents, flavorings, seasonings, eggs, milk, and so forth.

EXAMPLE NUMBER 40: CASSAVA DUMPLINGS

Combine 286 g cassava flour, 226.5 g water, until smooth and creamy, add 16 g cassava baking powder and mix well. Let dough set for about 15 minutes. Drop teaspoon-sized portions of batter into about 2 liters of rapidly boiling water or broth, may be thickened. Allow to remain in boiling water 2-6 minutes, preferably 5 minutes. If dumplings remain in boiling broth longer, dumplings will dissolve. When done, dumplings will be light and tender on the inside.

EXAMPLE NUMBER 41: CASSAVA BATTER

A batter prepared by the method of Example 33 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 42: CASSAVA CREPES

In yet another embodiment of the batter prepared in Example 33, the batter may be used to make a crepe-like product. The batter may be diluted by the addition of 10-400 g water, preferably 100 g to make a crepe-like product. The batter is spread in very thin layers on a cooking surface, and prepared according to the accepted convention.

EXAMPLE NUMBER 43: CASSAVA PIE CRUST

Mix thoroughly, 143 g cassava flour, 50 g oil, 56.8 g water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery. Cassava pie crust may be used as a double or single crust pie, with any type of filling, including meat (e.g., chicken pot pie) or fruit filling. For a baked pie crust, bake for 10 minutes at 350° F.

Although above ingredients are preferred, cassava flour may be used with shortening or lard and any other conventional ingredients. For example, when using lard, use about 100 g and decrease water to 10–14 g. Dough will seem stiff and hard, but will be just right after baking.

EXAMPLE NUMBER 44: CASSAVA TORTILLAS, CHIPS

Mix 143 g cassava flour with 85.2 g boiling water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 45: CASSAVA PRETZELS

Doughs produced by the processes described in Examples 44 and 45 may be used in processes of shaping to form pretzels of various sizes, coating with oil (optional), cooking by various processes of the art including but not limited to baking, frying, and drying to produce pretzels of varying sizes.

EXAMPLE 46: CASSAVA IMITATION NUT BUTTER 72 grams of cassava flour are placed into any blending equipment suitable for mixing very thick doughs at very high speeds, to which is added 200–250 g edible fatty material, such as vegetable oils (preferred for hypoallergenic products) but could also include other fatty materials. Add to this a paste made of 28.4 g water and 4.45 g cassava flour that have been cooked until gelatinized. The materials are throughly mixed for about 2 minutes or until the entire mixture is well blended, and the consistency of peanut butter.

EXAMPLE 47: CASSAVA IMITATION MAYONNAISE

Combine 43.16 g cassava flour, 6.5 g salt, and 113.25 g cold water until well blended. Add slowly to 340 g boiling water, stirring constantly. Continue stirring, while maintaining temperature at 50 to 150° C., until mixture is completely gelatinized and thickened. Cool. Place mixture in conventional high speed blending device; add 200 g oil, (optional: 21.3 g lemon juice, vinegar, or ascorbic acid solution). Mix materials on highest speed until well blended, smooth, and uniform consistency. Mayonnaise will thicken as it cools.

EXAMPLE NUMBER 48: CASSAVA MILK

Combine 453 g water and 71.5 g cassava flour, mix thoroughly. Stirring constantly, heat until well gelatinized, thick, and well blended. Blend together an additional 453 g water, 71.5 g very finely comminuted cassava flour, and 4.17 g oil in any high speed blending device. Add in the cooked flour mixture. Blend 1–30 minutes at highest speeds, preferably 4 minutes. May be strained if flour not sufficiently fine.

EXAMPLE NUMBER 49: CASSAVA MILK SHAKE

Combine 71.5 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50° F. or lower, preferably 35° F. In high speed blending device, combine gelatinized mixture, 12.5 g oil, 71.5 g cassava flour, and 113 g crushed ice. Blend well at speeds high enough to partially freeze mixture as ice particles become crushed and fine to form a thick slurry the consistency of a milk shake. The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 152.4 g flour, 453 g water and 12.5 g oil (½ water and flour still cooked as described above) under conditions of simultaneous freezing and mixing to form a milk shake-like slurry without adding crushed ice. Similarly other methods of the art may be used to produce the frozen slurry.

EXAMPLE NUMBER 50: CASSAVA ICE CREAM

The milk shake-like product described in Example 49 may be used as a base for ice cream products. The above slurry is subjected to freezing from 32° F. to −30° F. or lower, preferably −200° F., until product attains this temperature. Frozen mixture is then comminuted, and placed in high speed blending equipment and blended at highest speeds until well mixed, smooth, and creamy. Freezing, comminuting and mixing cycles may be repeated as desired, 2 such cycles are preferred. Additional embodiments described in Example 21 may also be used in this example.

EXAMPLE NUMBER 51: CASSAVA NOODLES

Using conventional equipment for kneading thick dough, combine 572 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g cassava flour and 120 g water may be cooked to a thick paste and added to the above mixture. In another alternative process, prior to extruding, the flour mixture described above which may or may not be simultaneously kneaded, may be maintained at temperatures above 50° C. for 2–30 minutes, preferably 2–5 minutes at 95° C. to gelatinize part of all of the dough.

When cooking, immerse noodles in boiling water for 2–10 minutes depending on width of noodles. Any other cooking techniques of the art may also be used. Noodles may be used in any type pasta dish—soups, stews, pasta and sauce dishes, and the like.

EXAMPLE NUMBER 52: CASSAVA CRACKERS

In any suitable machine for mixing heavy doughs, combine 572 g cassava flour, 340 g water. 3.25 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like. Alternatively, omit oil, or oil and salt, increasing water by 30 grams.

EXAMPLE 53: CASSAVA PUDDING

Combine equal parts by volume of cooked, mashed cassava and water, using 113.25 g of each. The method of cooking and pureeing may be by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are blended to a thick paste by any conventional means. Separately 4.45 g cassava flour is combined with 28.4 g water and heated to boiling point for 5 minutes to produce a thick gelatinized paste. The gelatinized paste is combined with the cooked tuber paste by any conventional mixing technique until well blended. The mixture is the consistency of pudding, and with the addition of no other ingredients has a pleasant sweet taste. This is not to preclude the use of other ingredients commonly used as ingredients in pudding such as eggs, milk, conventional flours, oil, sweeteners, flavorants, spices, seasonings, of any kind in this invention or cook 226.5 g water and 16.18 g cassava flour until gelatinized and thickened. Cool.

EXAMPLE 54: CASSAVA FLOUR

Thinly peel entire, untrimmed cassava tubers under running water, also removing any spots and/or, undesirable areas, but retaining the inner portion of the peel, and the woody parts of the tuber, including the woody ends of the tubers. Then free of excess water, dip briefly in distilled water, again remove excess. Do not soak. Shred to desired size, place on glass or metal trays; air dry at 145° F. for 8–12 hours, preferably 10 hours. Comminute shreds with any desired technique that utilizes most of the fiber, 100% utilization is preferred, to produce a flour product that is a fine flour of relatively uniform particle size distribution.

EXAMPLE 55: COOKED CASSAVA FLOUR

Cassava and other tubers are processed by the method of Example 54, with the added step of partially or completely gelatinizing the tubers as a separate step or in combination with other process steps.

EXAMPLE NUMBER 56: MALANGA BREAD

Place 453 g malanga flour in a suitable conventional mixing device. Slowly add 566 g water while mixing at lowest speed. When well blended, mix at highest speed for about 1 minute. Stir in 35.4 g baking powder; then mix at high speed for 15 seconds. As fast as possible pour into baking pan. Carefully place in oven heated to 425° F. and bake for 40 minutes. The amount of water needed varies with the moisture content and particle size of the flour. More coarse flour and/or flour with a lower moisture content will require more water. The resultant malanga bread product may be used in any way wheat bread is used.

EXAMPLE NUMBER 57: MALANGA IMITATION CORNBREAD

Ingredients: 453 g malanga flour, 566.25 g water, 35.4 g malanga baking powder. Combine above ingredients with baking powder added last; mix well, at highest speed with conventional mixing equipment until well blended and uniform consistency, about 1 minute. Transfer quickly into suitable baking container and bake 30–40 minutes at 425° F. Alternatively, the following proportions may be used in an imitation cornbread with honey or other liquid sweetener: 453 g malanga flour, 566 g water, 150 g honey, 35.4 g malanga baking powder. This product is used in the production of cake doughs.

EXAMPLE NUMBER 58: MALANGA MUFFINS

Combine 453 g malanga flour, 566 g water 12.5 g oil, 35.4 g malanga baking powder and mix well, at high speed with conventional techniques of the art until smooth and well blended. Add baking powder and mix well. Pour quickly or transfer by other means into suitable baking equipment. Bake for 20–25 minutes at 425° F.

EXAMPLE NUMBER 59: MALANGA PANCAKES

The following ingredients: 336.9 g malanga flour, 453 g water, 6.5 g salt, 50 g oil, 8 g malanga baking powder, are combined and mixed well on highest speed, preferably 1–2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color.

EXAMPLE NUMBER 60: MALANGA PANCAKE MIX

To provide an example of a dry mix-type product, malanga pancake mix is used. A malanga pancake mix product can be made by combining ingredients: 453 g flour, 87 g salt, and 10.7 g malanga baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of malanga pancake mixes.

EXAMPLE NUMBER 61: MALANGA PIZZA DOUGH

The batters described in Example 59 may also be used as a pizza dough. Prepare batter as described above, pour dough onto pizza pan. Place in oven and bake at 425 degrees until dough is almost done but still tacky on the top, about 20 minutes. Add any desired ingredients, various meats, vegetables, spices, and other materials common to the art. Bake until dough is completely done and ingredients thoroughly cooked, about 10 minutes.

Alternatively, the topping can be placed on the batter before cooking begins, or after cooking ends. Alternatively, the dough described for pie crust, Example 69, may be used as a pizza dough. The dough is prepared as described in the example, the dough is rolled out to the desired length, width, and thickness, toppings of any kind are added and the mixture is baked at 350° F. for 10–30 minutes.

EXAMPLE NUMBER 62: MALANGA WAFFLES

The following ingredients are combined by the method described above in Example 60: 336.9 g malanga flour, 453 g water, 6.5 g salt, 50 g oil, 8 g malanga baking powder. Pour batter into waffle iron or other suitable molding or shaping device preheated to 300–500° F. Watch for steam coming from the waffle iron as the waffles cook. Leave waffle iron closed as long as steam can be seen rising from the waffle iron. When steam stops, all water has been baked out of the batter and waffles are done, 5–10 minutes or more. When done the waffles should be golden brown in color.

EXAMPLE NUMBER 63: MALANGA FRENCH TOAST

Combine 21 g malanga flour, 3.25 g salt, and 297.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified. Alternatively, cook 226.5 g water and 21 g malanga flour until well gelatinized and thickened. Coat pieces of malanga bread. Fry to slightly browned and crusty in lightly greased griddle or skillet preheated to medium high. Alternatively french toast batter may be prepared by the method as described above without cooking the flour/water mixture. French toast batter may be used for many combinations with malanga bread crumbs and many other coating materials or alone.

EXAMPLE NUMBER 64: MALANGA COOKIES

Combine and mix well by the conventional art: 505.4 g malanga flour, 210.6 g water. 6.5 g salt. 150 g oil. 18 g malanga baking powder. Form into cookie shapes by the conventional art, preferably very thin. Bake at 350° F. on ungreased surface for 8–10 minutes, or until a light golden brown on the underside. Alternatively, add toppings as desired to the unbaked or baked dough. Any desired fruit, nut, flavors, seasonings of the conventional art may also be used. When a liquid sweetener or honey is used, the following ingredients are combined as described above: 505.4 g malanga flour, 170 g water, 1.6 g salt, 150 g honey, 150 g oil, 18 g malanga baking powder.

EXAMPLE NUMBER 65: MALANGA DOUGHNUTS, PRETZELS, HUSH PUPPIES, DOUGHNUT HOLES

From batter prepared in the method of Example 59, extrude batter through a doughnut press or any other desired device in rings onto hot oil; batter may also be dropped in balls, long pieces, even pretzel shapes. Temperature of the oil should be about 300–500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, etc. Alternatively, doughnuts may be preparations of conventional ingredients including but not limited to: other flours, extenders, binders, fillers, preserving agents, flavorings, seasonings, eggs, milk, and so forth.

EXAMPLE NUMBER 66: MALANGA DUMPLINGS

Prepare a dumpling batter in the method of Example 60. Let dough set for about 15 minutes. Drop teaspoon-sized portions of batter into about 2 liters of rapidly boiling water or broth, may be thickened. Allow to remain in boiling water 2–6 minutes, preferably 5 minutes. If dumplings remain in boiling broth longer, dumplings will dissolve. When done, dumplings will be light and tender on the inside.

EXAMPLE NUMBER 67: MALANGA BATTER

A batter prepared by the method of Example 59 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 68: MALANGA CREPES

In yet another embodiment of the batter prepared in Example 59, the batter may be used to make a crepe-like product. The batter may be diluted by the addition of 10–400 g water, preferably 100 g to make a crepe-like product. The batter is spread in very thin layers on a cooking surface, and prepared according to the accepted convention.

EXAMPLE NUMBER 69: MALANGA PIE CRUST

Mix thoroughly, 168.5 g malanga flour, 50 g oil, 170 g boiling water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery. Malanga pie crust may be used as a double or single crust pie, with any type of filling, including meat (e.g., chicken pot pie) or fruit filling. For a baked pie crust, bake for 10 minutes at 350° F.

Although above ingredients are preferred, malanga flour may be used with shortening or lard and any other conventional ingredients. For example, when using lard, use about 100 g and decrease water to 10–14 g. Dough will seem stiff and hard, but will be just right after baking.

EXAMPLE NUMBER 70: MALANGA TORTILLAS, CHIPS

Mix 168.5 g malanga flour with 170 g water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 71: MALANGA PRETZELS

Doughs produced by the processes described in Examples 69 and 70 may be used in processes of shaping to form pretzels of various sizes, coating with oil (optional), cooking by various processes of the art including but not limited to baking, frying, and drying to produce pretzels of varying sizes.

EXAMPLE 72: MALANGA IMITATION NUT BUTTER 453 grams of malanga flour are placed into any blending equipment suitable for mixing very thick doughs at very high speeds, to which is added 170–225 g edible fatty material, such as vegetable oils (preferred for hypoallergenic products) but could also include other fatty materials, and a gelatinized paste produced by cooking 21 g malanga flour and 113.25 g water. The materials are throughly mixed for about 2 minutes or until the entire mixture is well blended, and the consistency of peanut butter.

EXAMPLE 73: MALANGA IMITATION MAYONNAISE

Combine 52.6 g malanga flour 6.5 g salt, and 113.25 g cold water until well blended. Add slowly to 340 g boiling water, stirring constantly. Continue stirring until mixture is completely gelatinized and thickened. Place mixture in conventional high speed blending device; add 200 g oil, and optional: 21.3 g lemon Juice, vinegar, or ascorbic acid solution. Mix materials on highest speed until well blended, smooth, and uniform consistency. Mayonnaise will thicken as it cools.

EXAMPLE NUMBER 74: MALANGA MILK

Combine 453 g water and 42.1 g malanga flour, mix thoroughly. Stirring constantly, heat until well gelatinized, thick, and well blended. Blend together an additional 453 g water, 126.3 g very finely comminuted malanga flour, and 18.7 g oil in any high speed blending device. Add in the cooked flour mixture. Blend 1–30 minutes at highest speeds, preferably 4 minutes. May be strained if flour not sufficiently fine.

EXAMPLE NUMBER 75: MALANGA NOODLES

Using conventional equipment for kneading thick dough, combine 453 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g malanga flour and 120 g water may be cooked to a thick paste and added to the above mixture. In another alternative process, prior to extruding, the flour mixture described above which may or may not be simultaneously kneaded, may be maintained at temperatures above 50° C. for 2–30 minutes, preferably 2–5 minutes at 95° C. to gelatinize part of all of the dough.

When cooking, immerse noodles in boiling water for 2–10 minutes depending on width of noodles. Any other cooking techniques of the art may also be used. Noodles may be used in any type pasta dish—soups, stews, pasta and sauce dishes, and the like.

EXAMPLE NUMBER 76: MALANGA CRACKERS

In any suitable machine for mixing heavy doughs, combine 453 g malanga flour, 340 water, 6.5 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like. Alternatively, omit oil, or oil and salt, increasing water by 30 grams.

EXAMPLE 77: MALANGA PUDDING

Combine equal parts by volume of cooked, mashed malanga and water, using 113.25 g of each. The method of cooking and pureeing may be by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are blended to a thick paste by any conventional means. Separately, 5.25 g malanga flour is combined with 28.4 g water and heated to boiling point for sufficient time to produce a thick, gelatinized paste. The gelatinized paste is combined with the cooked tuber paste by any conventional mixing technique until well blended. The mixture is the consistency of pudding, and with the addition of no other ingredients has a pleasant, sweet taste.

This is not to preclude the use of other ingredients commonly used as ingredients in pudding such as eggs, milk, conventional flours, oil, sweeteners, flavorants, spices, seasonings, of any kind in this invention.

Alternatively, combine 84.2 g malanga flour and 453 g water, heat the resultant mixture by any conventional means with stirring until the mixture is very thick and completely gelatinized. Place in high speed blending device and blend at highest setting for at least 5 minutes. Add 25 g oil and blend again for 1–2 minutes.

EXAMPLE 78 MALANGA FLOUR

Peel malanga under running water, also removing any spots and/or undersirable areas, then free of excess water, dip briefly in distilled water, again remove excess do not soak. Shred to desired size, place on glass or metal trays; air dry at 145° F. for 8–12 hours, preferably 10 hours. Comminute shreds with any desired technique that utilizes most of the fiber, 100% utilization is preferred, to produce a flour product that is a fine flour of relatively uniform particle size distribution.

EXAMPLE 79: COOKED MALANGA FLOUR

Malanga or other tubers are processed by the method of Example 78, with the added step of partially or completely gelatinizing the tubers as a separate step or in combination with other process steps.

EXAMPLE NUMBER 80: YAM BREAD

Place 453 g yam flour in a suitable conventional mixing device. Slowly add 623 g water and 3.25 g salt while mixing at lowest speed. When well blended mix, at highest speed for about 1 minute. Stir in 47 g baking powder; then mix at high speed for 15 seconds. As fast as possible pour into baking pan. Carefully place in oven heated to 425° F. and bake for 50 minutes. The amount of water needed varies with the moisture content and particle size of the flour. More coarse flour and/or flour with a lower moisture content will require more water. The resultant yam bread product may be used in any way wheat bread is used.

EXAMPLE NUMBER 81: YAM IMITATION CORNBREAD

Ingredients: 304.8 g yam flour, 453 g water, 23.6 g yam baking powder, 6.5 g salt, 12.5 g oil. Combine above ingredients with baking powder added last: mix well, at highest speed with conventional mixing equipment until well blended and uniform consistency, about 1 minute. Transfer quickly into suitable baking container and bake 20–25 minutes at 425° F. Alternatively, the following proportions may be used in an imitation cornbread with honey or other liquid sweetener: 343 g yam flour, 396.4 g water, 6.5 g salt, 75 g honey, 23.6 g yam baking powder, 12.5 g oil.

EXAMPLE NUMBER 82: YAM CAKE DOUGH 343 g yam flour, 396.4 g water, 90 g honey, 35 g oil, 35.4 g suitable leavening agent, may be combined in the processes described in Example 81. Dough may be baked as described in Example 81, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 83: YAM MUFFINS

Combine 343 g yam flour, 453 g water, 6.5 g salt, 12.5 g oil, 23.6 g yam baking powder and mix well, at high speed with conventional techniques of the art until smooth and well blended. Add baking powder and mix well. Pour quickly or transfer by other means into suitable baking equipment. Bake for 20–25 minutes at 425° F.

EXAMPLE NUMBER 84: YAM PANCAKES

The following ingredients: 169.9 g frozen cooked yam flour, maintained at freezing point 453 g rapidly boiling water, 0.5 g salt, 37.5 g oil, and 12 g yam baking powder, with baking powder added in after water, salt and oil are combined and mixed well on highest speed, preferably 5 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color. When honey or other liquid sweetener is used, the ingredients: 169.9 g yam flour, 453 g water, 0.5 g salt, 37.5 g honey, 25 g oil, 12 g yam baking powder, may be used in the process described above.

EXAMPLE NUMBER 85: YAM PANCAKE MIX

To provide an example of a dry mix-type product, yam pancake mix is used. A yam pancake mix product can be made by combining ingredients: 453 g flour, 87 g salt, and 10.7 g yam baking powder. Mix ingredients well in a rolling ball mill or other conventional means to form a dry mix. Pancakes can be made from this dry mix by the addition of water and water/oil mixtures. Alternatively, by conventions of the art, the pancake mix oils may also be added to the above ingredient mix to produce a dry mix that contains oils. Also, sweeteners, flavors, seasonings, binders, fillers, and so forth may be utilized in the production of yam pancake mixes.

EXAMPLE NUMBER 86: YAM PIZZA DOUGH

The batters described in Example 84 may also be used as a pizza dough. Prepare batter as described above, pour dough onto pizza pan. Place in oven and bake at 425 degrees until dough is almost done but still tacky on the top, about 20 minutes. Add any desired ingredients, various meats, vegetables, spices, and other materials common to the art. Bake until dough is completely done and ingredients thoroughly cooked, about 10 minutes. Alternatively, the topping can be placed on the batter before cooking begins, or after cooking ends. Alternatively, the dough described for pie crust, Example 94, may be used as a pizza dough. The dough is prepared as described in the example, the dough is rolled out to the desired length, width, and thickness, toppings of any kind are added and the mixture is baked at 350° F. for 10–30 minutes.

EXAMPLE NUMBER 87: YAM WAFFLES

The following ingredients are combined by the method described above in Example 84: 304.8 g yam flour, 509.6 g water, 6.5 g salt, 50 g oil, 3.6 g yam baking powder. Pour batter into waffle iron or other suitable molding or shaping device preheated to 300–500° F. Watch for steam coming from the waffle iron as the waffles cook. Leave waffle iron closed as long as steam can be seen rising from the waffle iron. When steam stops, all water has been baked out of the batter and waffles are done, 5–10 minutes or more. When done the waffles should be golden brown in color.

EXAMPLE NUMBER 88: YAM FRENCH TOAST

Combine 226.5 g water and 21.2 g flour. Heat by any desired convention to form a thick paste. Coat pieces of yam bread. Fry to slightly browned and crusty in lightly greased griddle or skillet preheated to medium high. Alternatively combine 21.2 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified. Coat pieces of yam bread. Fry to slightly browned and crusty in lightly greased griddle or skillet preheated to medium high. Alternatively french toast batter may be prepared by the method as described above without cooking the flour/water mixture. French toast batter may be used for many combinations with yam bread crumbs and many other coating materials or alone.

EXAMPLE NUMBER 89: YAM COOKIES

Combine and mix well on highest speed 1–10 minutes, preferably 2–3 minutes: 339.75 g yam flour, 453 g rapidly boiling water, 0.6 g salt, 125 g oil, 12 g yam baking powder. Form into cookie shapes by the conventional art. Bake at 400° F. on ungreased surface for 8–10 minutes, or until a light golden brown on the underside. Alternatively, add toppings as desired to the unbaked or baked dough. Any desired fruit, nut, flavors, seasonings of the conventional art may also be used. When a liquid sweetener or honey is used, the following ingredients are combined as described above: 339.75 g frozen yam flour, 453 g rapidly boiling water, 0.6 g salt, 75 g honey, 100 g oil, 12 g yam baking powder.

EXAMPLE NUMBER 90: YAM DOUGHNUTS, PRETZELS, HUSH PUPPIES, DOUGHNUT HOLES

From batter prepared in the method of Example 84, extrude batter through a doughnut press or any other desired device in rings onto hot oil: batter may also be dropped in balls, long pieces, even pretzel shapes. Temperature of the oil should be about 300–500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, etc. Alternatively, doughnuts may be preparations of conventional ingredients including but not limited to: other flours, extenders, binders, fillers, preserving agents, flavorings, seasonings, eggs, milk, and so forth.

EXAMPLE NUMBER 91: YAM DUMPLINGS

Combine 152.4 g yam flour, 226.5 g water, 4.9 g salt, 12 g yam baking powder until smooth and creamy. Let dough set for about 15 minutes. Drop teaspoon-sized portions of batter into about 2 liters of rapidly boiling water or broth may be thickened. Allow to remain in boiling water 2-6 minutes, preferably 5 minutes. If dumplings remain in boiling broth longer, dumplings will dissolve. When done, dumplings will be light and tender on the inside.

EXAMPLE NUMBER 92: YAM BATTER

A batter prepared by the method of Example 84 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 93: YAM CREPES

In yet another embodiment of the batter prepared in Example 84, the batter may be used to make a crepe-like product. The batter may be diluted by the addition of 10–400 g water, preferably 100 g to make a crepe-like product. The batter is spread in very thin layers on a cooking surface, and prepared according to the accepted convention.

EXAMPLE NUMBER 94: YAM PIE CRUST

Mix thoroughly, 169.9 g yam flour, 50 g oil, 85.2 g water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery. Yam pie crust may be used as a double or single crust pie, with any type of filling, including meat (e.g., chicken pot pie) or fruit filling. For a baked pie crust, bake for 10 minutes at 350° F.

Although above ingredients are preferred, yam flour may be used with shortening or lard and any other conventional ingredients. For example, when using lard, use about 100 g and decrease water to 10–14 g. Dough will seem stiff and hard, but will be just right after baking.

EXAMPLE NUMBER 95: YAM TORTILLAS, CHIPS

Mix 169.9 g yam flour with 85 g boiling water; knead until well blended and very thick. By any desired conventional means achieve the shapes and sizes of tortillas or chips, bake at 350° F. for 10 minutes. When fried without oil, heat on medium high heat until slightly browned on both sides; turn as needed. When fried in hot oil, fry until crisp.

EXAMPLE NUMBER 96: YAM PRETZELS

Doughs produced by the processes described in Examples 94 and 95 may be used in processes of shaping to form pretzels of various sizes, coating with oil (optional), cooking by various processes of the art including but not limited to baking, and drying to produce pretzels of varying sizes.

EXAMPLE NUMBER 97: YAM IMITATION NUT BUTTER 453 grams of yam flour are placed into any blending equipment suitable for mixing very thick doughs at very high speeds, to which is added 150–200 g edible fatty material, such as vegetable oils (preferred for hypoallergenic products) but could also include other fatty materials. The materials are throughly mixed for about 2 minutes or until the entire mixture is well blended, and the consistency of nut butter. After several weeks of storage oil and flour will begin to separate, but is recombined very easily. Alternatively, the mixture may be heated until the yam flour is partially gelatinized to produce an imitation nut butter that separates less easily.

EXAMPLE NUMBER 98: YAM IMITATION MAYONNAISE

Combine 53.1 g yam flour, and 453 g cold water until well blended. Continue stirring, while maintaining temperature at 50 to 150° C., until mixture is completely gelatinized and thickened. Place mixture in conventional high speed blending device; add 200 g oil, and optional: 21.3 g lemon juice, vinegar, or ascorbic acid solution. Mix materials on highest speed until well blended, smooth, and uniform consistency. Mayonnaise will thicken as it cools.

EXAMPLE NUMBER 99: YAM MILK

Combine 906 g water and 169.9 g yam cooked flour, and 12.5 g oil, mix thoroughly. Blend 1-30 minutes at highest speeds, preferably 4 minutes. May be strained if flour not sufficiently fine.

EXAMPLE NUMBER 100: YAM MILK SHAKE

Combine 76.2 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50° F. or lower, preferably 35° F. In high speed blending device, combine gelatinized mixture, 12.5 g oil, 76.2 g yam flour, and 226.5 g crushed ice. Blend well at speeds high enough to partially freeze mixture as ice particles become crushed and fine to form a thick slurry the consistency of a milk shake. The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 152.4 g flour, 453 g water and 12.5 g oil (1/2 water and flour still cooked as described above) under conditions of simultaneous freezing and mixing to form a milk shake-like slurry without adding crushed ice. Similarly other methods of the art may be used to produce the frozen slurry.

EXAMPLE NUMBER 101: YAM ICE CREAM

The milk shake-like product described in Example 100 may be used as a base for ice cream products. The above slurry is subjected to freezing from 32° F. to −30° F. or lower, preferably −200–0° F., until product attains this temperature. Frozen mixture is then comminuted, and placed in high speed blending equipment and blended at highest speeds until well mixed, smooth, and creamy. Freezing, comminuting and mixing cycles may be repeated as desired, 2 such cycles are preferred. Additional embodiments described in Example 100 may also be used in this example.

EXAMPLE NUMBER 102: YAM NOODLES

Using conventional equipment for kneading thick dough, combine 453 g frozen flour from cooked tubers and 453 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g yam flour and 120 g water may be cooked to a thick paste and added to the above mixture. In another alternative process, prior to extruding, the flour mixture described above which may or may not be simultaneously kneaded, may be maintained at temperatures above 50° C. for 2-30 minutes, preferably 2-5 minutes at 95° C. to gelatinize part of all of the dough.

When cooking, immerse noodles in boiling water for 30 seconds. Any other cooking techniques of the art may also be used. Noodles may be used in any type pasta dish—soups, stews, pasta and sauce dishes, and the like.

EXAMPLE NUMBER 103: YAM CRACKERS

In any suitable machine for mixing heavy doughs, combine 453 g flour of cooked yam flour, 6.5 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like. Alternatively, omit oil, or oil and salt, increasing water by 30 grams.

EXAMPLE 104: YAM PUDDING

Combine equal parts of cooked, mashed yam paste and water, using 113.25 g each. The method forming the paste involves processes of cooking and pureeing by any conventional means including but not limited to steam heat, boiling and pressure cooking. The preferred method involves subjecting the peeled or unpeeled raw tubers, peeled tubers are preferred, to application of steam until all starch particles are gelatinized. The gelatinized tubers are blended to a thick paste by any conventional means. Separately 5.3 g yam flour is combined with 28.2 g water and heated to boiling point for 5 minutes to produce a thick gelatinized paste. The gelatinized paste is combined with the cooked tuber and water mixture by any conventional mixing technique until well blended. The mixture is the consistency of pudding, and with the addition of no other ingredients has a pleasant, sweet taste. This is not to preclude the use of other ingredients commonly used as ingredients in pudding such as eggs, milk, conventional flours, oil, sweeteners, flavorants, spices, seasonings, of any kind in this invention.

Alternatively, 226 g water and 21.2 g flour may be heated until starchy materials are gelatinized, and pureed with conventional techniques until smooth and well blended. Cool to 0-20° C., preferably 5-10° C., when forms pudding consistency.

EXAMPLE NUMBER 105: UNCOOKED FLOUR OF YAM

Peel yam tubers and pulverize, comminute, puree, or otherwise prepare yams for dehydration which is accomplished by low temperature techniques such as freeze drying or vacuum-drying techniques. The dried tubers are comminuted in a shear mill or the like to a fine flour by freezing the dried tubers or tuber pieces, and substantially into a fine flour in short pulses, so as to avoid heating the flour high enough to cause a strong flavor or bitter taste. Many other techniques for comminuting are possible. The whole or shredded, peeled tuber is incorporated into the flour, including most fibrous material preferably 100% of the fiber, to produce a flour product that is a fine flour of relatively uniform particle size distribution.

EXAMPLE 106: FLOUR OF COOKED TUBERS OF YAM

The tubers are peeled, and the like while being held under running water. They are then rinsed in distilled water, cut into cubes of any size, preferably 2×2×2, and subjected to heat with steam until thoroughly gelatinized. The tubers are then trimmed to remove all black, grey, or otherwise discolored sections shredded, and dried by low temperature means. The dried product is then comminuted to flours of various particle size distribution in any conventional grinding process that does not elevate the flour temperature above 100° C. Preferably, the entire tuber is ground including fibrous particles.

EXAMPLE NUMBER 107: AMARANTH BREAD

Place 560.4 g amaranth flour in a suitable conventional mixing device. Slowly add 226.5 g water, 3.25 g salt, and 100 g oil while mixing at lowest speed. When well blended mix, at highest speed for about 1 minute. Stir in 47 g baking powder; then mix at high speed for 15 seconds. Dough will be very stiff. Carefully place in oven heated to 425° F. and bake for 35 minutes. The amount of water needed varies with the moisture content and particle size of the flour. More coarse flour and/or flour with a lower moisture content will require more water. The resultant amaranth bread product may be used in any way wheat bread is used.

EXAMPLE NUMBER 108: AMARANTH IMITATION CORNBREAD

Ingredients: 560.4 g amaranth flour, 226.5 g water, 47 g amaranth baking powder, 3.25 g salt, 100 g oil. Combine above ingredients with baking powder added last; mix well, at highest speed with conventional mixing equipment until well blended and uniform consistency, about 1 minute. Transfer quickly into suitable baking container and bake 20-25 minutes at 425° F. Alternatively, the following proportions may be used in an imitation cornbread with honey or other liquid sweetener: 560.4 g amaranth flour, 226.5 g water, 3.25 g salt, 75 g honey, 47 g amaranth baking powder, 50 g oil.

EXAMPLE NUMBER 109: AMARANTH CAKE DOUGH 560.4 g amaranth flour, 226.5 g water, 90 g honey, 35 g oil, 47 g suitable leavening agent, may be combined in the processes described in Example 108. Dough may be baked as described in Example 108, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 110: AMARANTH MUFFINS

Combine 560.4 g amaranth flour, 226.5 g water, 3.25 g salt 100 g oil, and mix well, at high speed with conventional techniques of the art until smooth and well blended. Add 47 g baking powder and mix well. Pour quickly or transfer by other means into suitable baking equipment. Bake for 20-35 minutes at 425° F.

EXAMPLE NUMBER 111: AMARANTH PANCAKES

The following ingredients: 280.3 g amaranth flour, 226.5 g water, 6.5 g salt, 50 g oil, 16 g amaranth baking powder, are combined and mixed well on highest speed, preferably 1-2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color. When honey or other liquid sweetener is used, the ingredients: 280.3 g amaranth flour, 226.5 g water, 6.5 g salt, 37.5 g honey. 25 g oil, 16 g amaranth baking powder, may be used in the process described above.

EXAMPLE NUMBER 112: AMARANTH PANCAKE MIX

To provide an example of a dry mix-type product, amaranth pancake mix is used. An amaranth pancake mix product can be made by combining ingredients: 560.4 g flour, 8.7 g salt, and 10.7 g amaranth baking powder. Mix ingredients well in a rolling ball mill or other conventional means to form a dry mix. Pancakes can be made from this dry mix by the addition of water and water/oil mixtures. Alternatively, by conventions of the art, the pancake mix oils may also be added to the above ingredient mix to produce a dry mix that contains oils. Also, sweeteners, flavors, seasonings, binders, fillers, and so forth may be utilized in the production of amaranth pancake mixes.

EXAMPLE NUMBER 113: AMARANTH WAFFLES

The following ingredients are combined by the method described above in Example 111: 140.1 g amaranth flour, 85 g water, 16 g salt, 12.5 g oil, 4 g amaranth baking powder. Pour batter into waffle iron or other suitable molding or shaping device preheated to 300-500° F. Watch for steam coming from the waffle iron as the waffles cook. Leave waffle iron closed as long as steam can be seen rising from the waffle iron. When steam stops, all water has been baked out of the batter and waffles are done, 5-10 minutes or more. When done the waffles should be golden brown in color.

EXAMPLE NUMBER 114: AMARANTH FRENCH TOAST

Combine 52.6 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified, or cook 226.5 g water and 17.5 g flour by any conventional method until gelatinized. Coat pieces of amaranth bread. Fry to slightly browned and crusty in lightly greased griddle or skillet preheated to medium high. Alternatively french toast batter may be prepared by the method as described above without cooking the flour/water mixture. French toast batter may be used for many combinations with amaranth bread crumbs and many other coating materials or alone.

EXAMPLE NUMBER 115: AMARANTH

Combine and mix well by the conventional art: 560.6 g amaranth flour, 226.5 g water, 1.6 g salt, 100 g oil, 16 g amaranth baking powder. Form into cookie shapes by the conventional art. Bake at 350° F. on ungreased surface for 10-15 minutes, or until a light golden brown on the underside. Alternatively, add toppings as desired to the unbaked or baked dough. Any desired fruit, nut, flavors, seasonings of the conventional art may also be used. When a liquid sweetener or honey is used, the following ingredients are combined as described above: 560.6 g amaranth flour, 226.5 g water, 6.5 g salt, 75 g honey, 50 g oil, 16 g amaranth baking powder.

EXAMPLE NUMBER 116: AMARANTH DOUGHNUTS, PRETZELS, HUSH PUPPIES, DOUGHNUT HOLES

From batter prepared in the method of Example 111, extrude batter through a doughnut press or any other desired device in rings onto hot oil; batter may also be dropped in balls, long pieces, even pretzel shapes. Temperature of the oil should be about 300-500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, etc. Alternatively, doughnuts may be preparations of conventional ingredients including but not limited to: other flours, extenders, binders, fillers, preserving agents, flavorings, seasonings, eggs, milk, and so forth.

EXAMPLE NUMBER 117: AMARANTH DUMPLINGS

Combine 140.1 g amaranth flour, 56.8 g water, 16 g amaranth baking powder, and 50 g oil, until smooth and creamy. Let dough set for about 15 minutes. Drop teaspoon-sized portions of batter into about 2 liters of rapidly boiling water or broth, may be thickened. Allow to remain in boiling water 1-2 minutes, preferably 1½ minutes. If dumplings remain in boiling broth longer, dumplings will dissolve. When done, dumplings will be light and tender on the inside.

EXAMPLE NUMBER 118: AMARANTH BATTER

A batter prepared by the method of Example 111 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 119: AMARANTH CREPES

In yet another embodiment of the batter prepared in Example 111, the batter may be used to make a crepe-like product. The batter may be diluted by the addition of 10-400 g water, preferably 100 g to make a crepe-like product. The batter is spread in very thin layers on a cooking surface, and prepared according to the accepted convention.

EXAMPLE NUMBER 120: AMARANTH PIE CRUST

Mix thoroughly, 140.1 g amaranth flour, 50 g oil, 56.8 g water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery. Amaranth pie crust may be used as a double or single crust pie, with any type of filling, including meat (e.g., chicken pot pie) or fruit filling. For a baked pie crust, bake for 10 minutes at 350° F.

Although above ingredients is preferred, amaranth flour may be used with shortening or lard and any other conventional ingredients. For example, when using lard, use about 100 g and decrease water to 10-14 g. Dough will seem stiff and hard, but will be just right after baking.

EXAMPLE NUMBER 121: AMARANTH TORTILLAS, CHIPS

Mix 140.1 g amaranth flour with 85.2 g water; knead until well blended and very thick. By any desired conventional means achieve the shapes and sizes of tortillas or chips. May be fried with or without oil, or baked. When fried without oil, heat on medium high heat until slightly browned on both sides., turn as needed. When fried in hot oil, fry until crisp. Alternatively, bake by conventional means until crisp.

EXAMPLE NUMBER 122: AMARANTH PRETZELS

Doughs produced by the processes described in Examples 120 and 121 may be used in processes of shaping to form pretzels of various sizes, coating with oil (optional), cooking by various processes of the art including but not limited to baking, frying, and drying to produce pretzels of varying sizes.

EXAMPLE 123: AMARANTH IMITATION NUT BUTTER 560.4 grams of amaranth flour are placed into any blending equipment suitable for mixing very thick doughs at very high speeds, to which is added 150-200 g edible fatty material, such as vegetable oils (preferred for hypoallergenic products) but could also include other fatty materials. The materials are throughly mixed for about 2 minutes or until the entire mixture is well blended, and the consistency of peanut butter. After several weeks of storage oil and flour will begin to separate, but is recombined very easily. Alternatively, the mixture may be heated until the amaranth flour is partially gelatinized to produce an imitation nut butter that separates less easily.

EXAMPLE 124: AMARANTH IMITATION MAYONNAISE

Combine 140.1 g amaranth flour, 3.25 g salt, and 170.4 g cold water in a pan and heat until thick while maintaining temperature at 50 to 150° C., until mixture is completely gelatinized and thickened. Place mixture in conventional high speed blending device; add 200 g oil, (optional: 21.3 g lemon juice, vinegar, or ascorbic acid solution). Mix materials on highest speed until well blended, smooth, and uniform consistency. Mayonnaise will thicken as it cools.

EXAMPLE NUMBER 125: AMARANTH MILK

Combine 906 g water and 140.1 g amaranth flour, 12.5 g oil. Blend together in any high speed blending device. Blend 1-30 minutes at highest speeds, preferably 4 minutes. May be strained if flour not sufficiently fine.

EXAMPLE NUMBER 126: AMARANTH NOODLES

Using conventional equipment for kneading thick dough, combine 560.4 g flour and 226.5 g water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g amaranth flour and 120 g water may be cooked to a thick paste and added to the above mixture.

In another alternative process, prior to extruding, the flour mixture described above which may or may not be simultaneously kneaded, may be maintained at temperatures above 50° C. for 2-30 minutes, preferably 2-5 minutes at 95° C. to gelatinize part of all of the dough.

When cooking, immerse noodles in boiling water for 2-10 minutes depending on width of noodles. Any other cooking techniques of the art may also be used. Noodles may be used in any type pasta dish—soups, stews, pasta and sauce dishes, and the like.

EXAMPLE NUMBER 127: AMARANTH CRACKERS

In any suitable machine for mixing heavy doughs, combine 560.4 g amaranth flour. 226.5 g water, 6.5 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20-25 minutes. Otherwise, cook by any convention of the art, including baking, frying and the like. Alternatively, omit oil, or oil and salt, increasing water by 30 grams.

EXAMPLE 128: AMARANTH PUDDING

Combine 226.5 g water. 70.1 g flour—cook in any conventional heating apparatus until mixture is gelatinized. Put in a high speed blender and blend until very smooth, about 5 minutes. Add 25 g oil, cool.

EXAMPLE NUMBER 129: AMARANTH FLOUR

Comminute amaranth seeds by any desired technique or combination of techniques common to the art to produce a meal. The meal is further ground, in as many repetitions and by such techniques as needed to comminute the meal to a flour of relatively uniform, fine particle size with most and preferably all of the seed incorporated into the flour.

EXAMPLE 130: COOKED AMARANTH FLOUR 100 g amaranth seed, meal, or flour is combined with 1000 g water and heated to about 200° F. for about 4 hours, with water added as necessary to form a soft, gelatinized mass. The mass is subjected to methods of pureeing, pulping, comminuting, pulverizing and the like to form a smooth, homogenous fluid or paste. This mixture is dried by suitable means of the art and comminuted to form a fine powder.

EXAMPLE NUMBER 131: LOTUS BREAD

Place 453 g lotus flour in a suitable conventional mixing device. Slowly add 679.5 g water and while mixing at lowest speed. When well blended mix, at highest speed for about 1 minute. Stir in 35.4 g baking powder; then mix at high speed for 15 seconds. As fast as possible pour into baking pan. Carefully place in oven heated to 400° F. and bake for 60 minutes. The amount of water needed varies with the moisture content and particle size of the flour. More coarse flour and/or flour with a lower moisture content will require more water. The resultant lotus bread product may be used in any way wheat bread is used.

EXAMPLE NUMBER 132: LOTUS IMITATION CORNBREAD

Ingredients: 453 g lotus flour, 679.5 g water, 35.4 g lotus baking powder. Combine above ingredients with baking powder added last; mix well, at highest speed with conventional mixing equipment until well blended and uniform consistency, about 1 minute. Transfer quickly into suitable baking container and bake 30-40 minutes at 425° F. Alternatively, the following proportions may be used in an imitation cornbread with honey or other liquid sweetener: 453 g lotus flour. 679.5 g water, 75 g honey, 35.4 g lotus leavening agent.

EXAMPLE NUMBER 133: LOTUS CAKE DOUGH 343 g lotus flour, 396.4 g water, 90 g honey, 35 g oil, 35.4 g suitable leavening agent, may be combined in the processes described in Example 132. Dough may be baked as described in Example 132, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 134: LOTUS MUFFINS

Combine 362.4 g lotus flour, 453 g water, 6.5 g salt, 75 g oil, and mix well, at high speed with conventional techniques of the art until smooth and well blended. Add 8 g leavening agent and mix well. Pour quickly or transfer by other means into suitable baking equipment. Bake for 20-25 minutes at 425° F.

EXAMPLE NUMBER 135: LOTUS PANCAKES

The following ingredients: 362.4 g lotus flour, 453 g water, 6.5 g salt, 75 g oil, are combined and mixed well on highest speed, preferably 1-2 minutes in high speed blending device. Put 8 g lotus leavening agent in last and mix again. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color. When honey or other liquid sweetener is used, the ingredients: 362.4 g lotus flour, 453 g water, 6.5 g salt, 75 g honey, 50 g oil, 8 g lotus leavening agent, may be used in the process described above.

EXAMPLE NUMBER 136: LOTUS PANCAKE MIX

To provide an example of a dry mix-type product, lotus pancake mix is used. A lotus pancake mix product can be made by combining ingredients: 362.4 g flour, 8.7 g salt, and 10.7 g lotus baking powder. Mix ingredients well in a rolling ball mill or other conventional means to form a dry mix. Pancakes can be made from this dry mix by the addition of water and water/oil mixtures. Alternatively, by conventions of the art, the pancake mix oils may also be added to the above ingredient mix to produce a dry mix that contains oils. Also, sweeteners, flavors, seasonings, binders, fillers, and so forth may be utilized in the production of lotus pancake mixes.

EXAMPLE NUMBER 137: LOTUS PIZZA DOUGH

The batters described in Example 135 may also be used as a pizza dough. Prepare batter as described above, pour dough onto pizza pan. Place in oven and bake at 425 degrees until dough is almost done but still tacky on the top, about 20 minutes. Add any desired ingredients, various meats, vegetables, spices, and other materials common to the art. Bake until dough is completely done and ingredients thoroughly cooked, about 10 minutes. Alternatively, the topping can be placed on the batter before cooking begins, or after cooking ends. Alternatively, the dough described for pie crust. Example 145. may be used as a pizza dough. The dough is prepared as described in the example, the dough is rolled out to the desired length, width, and thickness, toppings of any kind are added and the mixture is baked at 350° F. for 10-30 minutes.

EXAMPLE NUMBER 138: LOTUS WAFFLES

The following ingredients are combined by the method described above in Example 135: 362.4 g lotus flour, 453 g water, 6.5 g salt, 75 g oil, 8 g lotus leavening agent. Pour batter into waffle iron or other suitable molding or shaping device preheated to 300-500° F. Watch for steam coming from the waffle iron as the waffles cook. Leave waffle iron closed as long as steam can be seen rising from the waffle iron. When steam stops, all water has been baked out of the batter and waffles are done. 5-10 minutes or more. When done the waffles should be golden brown in color.

EXAMPLE NUMBER 139: LOTUS FRENCH TOAST

Combine 22.7 g flour, 3.25 g salt, and 226.5 g water and mix until smooth and homogenous. Heat by any desired convention until mixture is well gelatinized and thickened. Stir in 50 g oil. Pour mixture into high speed blending device; while blending at high speed, slowly drop in ground meat or other protein source and blend until meat is completely comminuted and liquified or use 226.5 g water and 22.7 g lotus flour that have been cooked until thick. Coat pieces of lotus bread. Fry to slightly browned and crusty in lightly greased griddle or skillet preheated to medium high. Alternatively french toast batter may be prepared by the method as described above without cooking the flour/water mixture. French toast batter may be used for many combinations with lotus bread crumbs and many other coating materials or alone.

EXAMPLE NUMBER 140: LOTUS COOKIES

Combine and mix well by the conventional art: 724.8 g lotus flour, 226.5 g water, 26 g salt, 300 g oil, 29.7 g lotus baking powder. Form into cookie shapes by the conventional art. Bake at 350° F. on ungreased surface for 10 minutes, or until a light golden brown on the underside. Alternatively, add toppings as desired to the unbaked or baked dough. Any desired fruit, nut, flavors, seasonings of the conventional art may also be used. When a liquid sweetener or honey is used, the following ingredients are combined as described above: 724.8 g lotus flour, 226.5 g water, 26 g salt, 75 g honey, 100 g oil, 29.7 g lotus leavening agent.

EXAMPLE NUMBER 141: LOTUS DOUGHNUTS, PRETZELS, HUSH PUPPIES, DOUGHNUT HOLES

From batter prepared in the method of Example 135, extrude batter through a doughnut press or any other desired device in rings onto hot oil; batter may also be dropped in balls, long pieces, even pretzel shapes. Temperature of the oil should be about 300-500 degrees. If the oil is hot enough the dough will float at the top of the oil. Fry doughnuts or other shapes until golden brown on all sides. Remove from oil, drain. Serve plain or top with fruit, honey, nuts, coconut, peanut butter, etc. Alternatively, doughnuts may be preparations of conventional ingredients including but no limited to: other flours, extenders, binders, fillers, preserving agents, flavorings, seasonings, eggs, milk, and so forth.

EXAMPLE NUMBER 142: LOTUS DUMPLINGS

Combine 362.4 g lotus flour, 453 g water, 6.5 g salt, 8 g lotus, leavening agent until smooth and creamy. Let dough set for about 15 minutes. Drop teaspoon-sized portions of batter into about 2 liters of rapidly boiling water or broth, may be thickened. Allow to remain in boiling water 10 minutes. If dumplings remain in boiling broth longer, dumplings will dissolve. When done, dumplings will be light and tender on the inside.

EXAMPLE NUMBER 143: LOTUS BATTER

A batter prepared by the method of Example 135 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 144: LOTUS CREPES

In yet another embodiment of the batter prepared in Example 135, the batter may be used to make a crepe-like product. The batter may be diluted by the addition of 10-400 g water, preferably 100 g to make a crepe-like product. The batter is spread in very thin layers on a cooking surface, and prepared according to the accepted convention.

EXAMPLE NUMBER 145: LOTUS PIE CRUST

Mix thoroughly, 181.2 g lotus flour, 50 g oil, 85.2 g boiling water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery. Lotus pie crust may be used as a double or single crust pie, with any type of filling, including meat (e.g., chicken pot pie) or fruit filling. For a baked pie crust, bake for 10 minutes at 350° F. Although above ingredients is preferred, lotus flour may be used with shortening or lard and any other conventional ingredients. For example, when using lard, use about 100 g and decrease water to 10-14 g. Dough will seem stiff and hard, but will be just right after baking.

EXAMPLE NUMBER 146: LOTUS TORTILLAS, CHIPS

Mix 181.2 g lotus flour with 142 g boiling water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 147: LOTUS PRETZELS

Doughs produced by the processes described in Examples 145 and 146 may be used in processes of shaping to form pretzels of various sizes, coating with oil (optional), cooking by various processes of the art including but not limited to baking, frying, and drying to produce pretzels of varying sizes.

EXAMPLE NUMBER 148: LOTUS IMITATION NUT BUTTER 453 grams of lotus flour are placed into any blending equipment suitable for mixing very thick doughs at very high speeds, to which is added 200-250 g edible fatty material,. such as vegetable oils (preferred for hypoallergenic products) but could also include other fatty materials. Add to this 28.4 g water and 5.5 g flour that have been cooked to a thick paste. The materials are throughly mixed for about 2 minutes or until the entire mixture is well blended, and the consistency of peanut butter.

EXAMPLE 149: LOTUS IMITATION MAYONNAISE

Combine 56.3 g lotus flour, 13 g salt, and 113.25 g cold water until well blended. Add slowly to 340 g boiling water, stirring constantly. Continue stirring, while maintaining temperature at 50 to 150° C., until mixture is completely gelatinized and thickened and cool. Place mixture in conventional high speed blending device; add 200 g oil, and (optional: 21.3 g lemon Juice, vinegar, or ascorbic acid solution). Mix materials on highest speed until well blended, smooth, and uniform consistency. Mayonnaise will thicken as it cools.

EXAMPLE NUMBER 150: LOTUS MILK

Combine 453 g water and 90.6 g lotus flour, mix thoroughly. Stirring constantly, heat until well gelatinized, thick, and well blended. Blend together an additional 453 g water, 90.6 g very finely comminuted lotus flour, and 12.5 g oil in any high speed blending device. Add in the cooked flour mixture. Blend 1-30 minutes at highest speeds, preferably 4 minutes. May be strained if flour not sufficiently fine.

EXAMPLE NUMBER 151: LOTUS MILK SHAKE

Combine 90.6 g flour and 226.5 g water in suitable mixing and heating apparatus. As mixture approaches boiling point, increase revolutions per minute. Continue rapid stirring while boiling for about 5 minutes. When thoroughly gelatinized, very thick, and smooth, cool to 50° F. or lower, preferably 35° F. In high speed blending device, combine gelatinized mixture, 12.5 g oil, 90.6 g lotus flour, and 226.5 g crushed ice. Blend well at speeds high enough to partially freeze mixture as ice particles become crushed and fine to form a thick slurry the consistency of a milk shake. The above milk shake-like product without further embodiments has a very pleasant taste, although any desired combination of fruits, nuts, sweeteners, flavorings, seasonings, spices, fillers, extenders, binders, and so forth may also be added to the product.

Alternatively, the milk shake-like product may be formed by 181.2 g flour, 453 g water and 12.5 g oil ($\frac{1}{4}$ water and flour still cooked as described above) under conditions of simultaneous freezing and mixing to form a milk shake-like slurry without adding crushed ice. Similarly other methods of the art may be used to produce the frozen slurry.

EXAMPLE NUMBER 152: LOTUS ICE CREAM

The milk shake-like product described in Example 151 may be used as a base for ice cream products. The above slurry is subjected to freezing from 32° F. to −30° F. or lower, preferably −200° F., until product attains this temperature. Frozen mixture is then comminuted, and placed in high speed blending equipment and blended at highest speeds until well mixed, smooth, and creamy. Freezing, comminuting and mixing cycles may be repeated as desired, 2 such cycles are preferred. Additional embodiments described in Example 151 may also be used in this example.

EXAMPLE NUMBER 153: LOTUS NOODLES

Using conventional equipment for kneading thick dough, combine 453 g flour and 340 g boiling water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g lotus flour and 120 g water may be cooked to a thick paste and added to the above mixture. In another alternative process, prior to extruding, the flour mixture described above which may or may not be simultaneously kneaded, may be maintained at temperatures above 50° C. for 2-30 minutes, preferably 2-5 minutes at 95° C. to gelatinize part of all of the dough.

When cooking, immerse noodles in boiling water for 2-10 minutes depending on width of noodles. Any other cooking techniques of the art may also be used. Noodles may be used in any type pasta dish—soups, stews, pasta and sauce dishes, and the like.

EXAMPLE NUMBER 154: LOTUS CRACKERS

In any suitable machine for mixing heavy doughs, combine 453 g lotus flour, 3.25 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350° F. for 20 minutes. Otherwise, cook by any convention of the art, including baking, frying and the like. Alternatively, omit oil, or oil and salt, increasing water by 30 grams.

EXAMPLE 155: LOTUS PUDDING

Combine equal parts by volume of cooked, mashed lotus and water, using 113.25 g of each. The method of cooking and pureeing may be by any conventional means including but not limited to steam heat, boiling and pressure cooking to application of steam until all starch particles are gelatinized. The gelatinized lotus are blended to a thick paste by any conventional means. Separately 5.65 g lotus flour is combined with 28.4 g water and heated to boiling point for 5 minutes to produce a thick gelatinized paste. The gelatinized paste is combined with the cooked tuber paste by any conventional mixing technique until well blended. The mixture is the consistency of pudding. Alternatively, cook 226.5 g water and 22.7 g lotus flour by any conventional method until gelatinized and cool. This is not to preclude the use of other ingredients commonly used as ingredients in pudding such as eggs, milk, conventional flours, oil, sweeteners, flavorants, spices, seasonings, of any kind in this invention.

EXAMPLE NUMBER 156: LOTUS FLOUR

Peel lotus under running water, also removing any spots and/or undesirable areas, then free of excess water. Dip briefly in distilled water, again remove excess water; do not soak. Shred to desired size, place on glass or metal trays: air dry at 145° F. for 8-12 hours, preferably 10 hours. Comminute shreds with any desired technique that utilizes most of the fiber, 100% utilization is preferred, to produce a flour product that is a fine flour of relatively uniform particle size distribution.

EXAMPLE NUMBER 157: COOKED LOTUS FLOUR

Lotus are processed by the method of Example 156, with the added step of partially or completely gelatinizing the tubers as a separate step or in combination with other process steps.

Having now fully described the invention, it will be apparent to one of ordinary skill in the art that many changes and modifications can be made thereto without departing from the spirit of the invention as set forth herein.

I claim:

1. A non-grain edible flour consisting essentially of the comminuted flesh of a tuber selected from the group consisting of tubers with light colored flesh of family Convolvulaceae; tubers of family Araceae, tubers of family Dioscoreaceae, tubers of family Nymphaeaceae, tubers of family Euphorbiaceae and tubers of family Alismataceae, dried to a moisture content of less than 20% by weight, wherein said flour contains at least 75% of the plant fiber and other non-farinaceous substance of the tuber, comminuted to a particle size such that the comminuted tuber will pass through a screen of 0.015 inch mesh.

2. The flour of claim 1 wherein the flour contains at least 90% of the plant fiber and other non-farinaceous substance of the tuber.

3. The flour of claim 1 wherein the flour contains substantially all of the plant fiber and other non-farinaceous substance of the tuber.

4. The flour of claim 1 wherein the entire flour passes through a screen of 0.001 inch mesh.

5. A milk substituted consisting essentially of the flour of claim 1 and water wherein the water and flour are present in proportions of 1:1 to 30:1 parts by volume of water per part by volume of flour.

6. An ice cream substitute formed by the process of freezing the milk substituted of claim 5.

7. The flour of claim 1 wherein the flour is uncooked.

8. The flour of claim 1 wherein the flour is at least partially gelatinized.

9. The flour of claim 1 wherein the flour is from the white sweet potato.

10. The flour of claim 9, wherein the white sweet potato is camote.

11. A baked product consisting essentially of the flour of claim 1 and water in an amount effective to product said baked product.

12. A colloidal product consisting essentially of the flour of claim 1, an oil, and water wherein the flour is present in an amount of 0.1-3 parts by weight; an the oil and water are each present in an amount of 1-15 parts by weight, which may be the same or different.

13. An imitation nut butter product consisting essentially of oil and the flour of claim 1 wherein the amount of oil in admixture with the flour in an amount effective to impart a nut butter texture.

14. A batter-type product consisting essential of the flour of claim 1, oil of comminuted tubers from the group consisting of Convulvulacaeae, Euphorbiaceae, Araceae, Dioscoreaceae, Nymphaeaceae, and Alismataceae, or a comminuted seed from family Amaranthaceae and Chenopodiaceae; the flour of the particle size such that the entire flour passes through a screen of 0.015 mesh;

an oil; and water in an amount effective to impart a batter consistency to said product.

15. A non-grain edible flour possessing the ability to hold a rise in the absence of grain flour, legume flour, or added fiber, dried to a moisture content of less than 20% by weight; said non-grain edible flour consisting essentially of comminuted particles of a tuber selected from the group consisting of tubers of light colored flesh of family Convolvulacaeae; tubers of family Araceae, tubers of family Dioscoreaceae, tuber of family Nymphaeaceae, tubers of family Euphorbiaceae and tubers of family Alismataceae, wherein said flour contains at least 75% of the plant fiber and other non-farinaceous substance of the tuber, comminuted to a particle size such that the comminuted tuber will pass through a screen of 0.015 inch mesh.

16. The flour of claim 15, wherein the flour is from cassava.

17. The flour of claim 15, wherein the tuber is selected from the group consisting of malanga, taro, and amorphophallus.

18. The flour of claim 15, wherein the flour is from tropical yams.

19. The flour of claim 15, wherein the flour is from lotus.

20. The flour of claim 15, wherein the flour is from arrowhead.

21. A baked product consisting essentially of the flour of claim 15 and water; wherein the flour is present in an amount of one part by weight; and the water is present in an amount of 0.5-4 parts by weight per unit of flour.

22. The flour of claim 15 mixed with water and formed into an extruded product.

23. A non-grain edible flour possessing the ability to hold a rise in the absence of grain flour, legume flour, or added fiber, dried to a moisture content of less than 20% by weight and consisting essentially of comminuted seeds selected from the group consisting of seeds of family Amaranthaceae and seeds or family Chenopodiaceae, wherein said flour contains at least 75% of the plant fiber and non-farinaceous substance of the seed, comminuted to a particle size such that the comminuted seeds will pass through a screen of 0.015 inch mesh.

24. The flour of claim 23 wherein the flour contains at least 90% of the plant fiber and other non-farinaceous substance of the seeds.

25. The flour of claim 30 wherein the flour contains substantially all of the plant fiber and other non-farinaceous substance of the seeds.

26. The flour of claim 23 wherein the flour is uncooked.

27. The flour of claim 23 wherein the flour is at least partially gelatinized.

28. The flour of claim 23 wherein the flour includes substantially all portions of the seeds.

29. The flour of claim 23 wherein the flour passes through a screen of 0.001 inch mesh.

30. A flour product of claim 23 wherein the flour is unsifted, and includes substantially all portions of the seeds.

31. The flour of claim 23, wherein the flour is from amaranth.

32. The flour of claim 23, wherein the flour is from quinoa.

33. An imitation nut butter product consisting essentially of oil and the flour of claim 23; wherein the amount of oil in admixture with the flour is sufficient to impart a nut butter texture.

34. A batter-type product consisting essentially of the flour of claim 23 and water in amounts effective to produce said batter-type product.

35. A baked product consisting essentially of the flour of claim 23 and water in amounts effective to produce said baked product.

36. A colloidal product consisting essentially of the flour of claim 23, an oil, and water in amounts effective to produce said colloidal product.

37. An extruded product consisting essentially of water and the flour of claim 23 in amounts effective to produce said extruded product.

38. A milk substituted consisting essentially of the flour of claim 23 and water in amounts effective to produce said milk substitute.

39. An ice cream substitute formed by the process which consists essentially of freezing the milk substituted of claim 38.

40. A non-grain edible flour possessing the ability to hold a rise in the absence of grain flour, legume flour, or added fiber, dried to a moisture content of less than 20% by weight consisting essentially of comminuted tubers of family Euphorbiaceae containing at least 50% of the plant fiber and other non-farinaceous substance of the tuber, comminuted to a size such that the comminuted tuber will pass through a screen of 0.015 inch mesh.

41. The flour of claim 40 wherein the entire flour passes through a screen of 0.001 inch mesh.

42. The flour of claim 40 wherein the flour is uncooked.

43. The flour of claim 40 wherein the flour is at least partially gelatinized.

44. A non-grain edible flour possessing the ability to hold a rise in the absence of grain flour, legume flour, or added fiber, dried to a moisture content of less than 20% by weight and consisting essentially of comminuted seeds selected from the group consisting of seeds of family Amaranthaceae and seeds of family Chenopodiaceae, wherein the flour contains at least 50% of the plant fiber and non-farinaceous substance of the seed, comminuted to a particle size such that the comminuted seed will pass through a screen of 0.015 inch mesh.

45. A method for making flour from a tuber selected from the group consisting of tubers of family Convolvulacaeae, tubers of family Araceae, tubers of family Dioscoreaceae, tubers of family Nymphaeaceae, tubers of family Euphorbiaceae and tubers of family Alismataceae which comprises the steps of; a) comminuting the tuber to a particle size of less than 0.015 inch; b) retaining most of the fiber and other non-farinaceous substance of the tuber; c) reducing the moisture content, and d) recovering a flour product of said tubers consisting essentially of less than 15% moisture, a particle size of less than 0.015 inch, and at least 75% of the plant fiber and other non-farinaceous substance of the tuber.

46. A method for making flour of tubers of family Euphorbiaceae which comprises the steps of: a) removing the outer cork layer of the peel, b) comminuting the tuber to a particle size of less than 0.015 inch, including the woody stem portions and inner layer of the peel; c) retaining most of the fiber and other non-farinaceous substance of the tuber, including fibrous material in the woody stem portions and inner layer of the peel; d) reducing the moisture content, and e) recovering a flour product of said tube consisting essentially of less than 15% moisture, a particle size of less than 0.015 inch, and at least 50% of the plant fiber and other non-farinaceous substance of the tuber.

47. A method for making flour of tubers of family Dioscoreaceae which comprises the steps of; a) drying the tuber at temperatures not greater than 50° F.; b) comminuting the tuber to a particle size of less than 0.015 inch at temperatures no greater than 50° F.; and c) recovering a non-bitter flour product consisting essentially of less than 15% moisture, a particle size of less than 0.015 inch, and at least 75% of the plant fiber and other non-farinaceous substance of the tuber.

48. The process of claim 47, wherein the step of comminuting is performed in intermittent steps to minimize heat formation.

49. A non-bitter tasting flour of family Dioscoreaceae formed by the process of claim 47.

50. A method for making flour from seeds of families Amaranthaceae and chenopodiaceae which comprises the steps of; a) comminuting the seed to a particle size of less than 0.015 inch; b) retaining most of the fiber and other non-farinaceous substance of the seeds; c) reducing the moisture content, and d) recovering a flour product consisting essentially of a particle size of less than 0.015 inch, and at least 75% of the plant fiber and other non-farinaceous substance of the seed.

* * * * *